United States Patent
Goldstein et al.

(10) Patent No.: US 10,025,653 B2
(45) Date of Patent: *Jul. 17, 2018

(54) COMPUTER ARCHITECTURE AND METHOD FOR MODIFYING INTAKE DATA RATE BASED ON A PREDICTIVE MODEL

(71) Applicant: Uptake Technologies, Inc., Chicago, IL (US)

(72) Inventors: Michael Goldstein, Chicago, IL (US); Tom Ravensberg, Chicago, IL (US); Will Hansmann, River Forest, IL (US)

(73) Assignee: Uptake Technologies, Inc., Chicago, IL (US)

( * ) Notice: Subject to any disclaimer, the term of this patent is extended or adjusted under 35 U.S.C. 154(b) by 45 days.

This patent is subject to a terminal disclaimer.

(21) Appl. No.: 14/963,212

(22) Filed: Dec. 8, 2015

(65) Prior Publication Data

US 2017/0161130 A1    Jun. 8, 2017

(51) Int. Cl.
*G06F 11/00*    (2006.01)
*G06F 11/07*    (2006.01)
*G06N 7/00*    (2006.01)

(52) U.S. Cl.
CPC ........ *G06F 11/079* (2013.01); *G06F 11/0721* (2013.01); *G06N 7/005* (2013.01)

(58) Field of Classification Search
CPC .... G06F 11/079; G06F 11/008; G06F 11/004; G06F 11/3058; G06F 11/3089;

(Continued)

(56) References Cited

U.S. PATENT DOCUMENTS 5,566,092 A    10/1996 Wang et al.
5,633,800 A    5/1997 Bankert et al.
(Continued)

FOREIGN PATENT DOCUMENTS

WO    2005094493 A2    10/2005
WO    2011117570    9/2011
(Continued)

OTHER PUBLICATIONS

Gu, Xiaohui et al., Toward Predictive Failure Management for Distributed Stream Processing Systems, 2008, IEEE, p. 825-832.*

(Continued)

*Primary Examiner* — Marc Duncan
(74) *Attorney, Agent, or Firm* — Lee Sullivan & Smith, LLP

(57) ABSTRACT

Disclosed herein is a computer architecture and software that is configured to modify data intake operation at an asset-monitoring system based on a predictive model. In accordance with the present disclosure, the asset-monitoring system may execute a predictive model that outputs an indicator of whether at least one event from a group of events (e.g., a failure event) is likely to occur at a given asset within a given period of time in the future. Based on the output of this predictive model, the asset-monitoring system may modify one or more operating parameters for ingesting data from the given asset, such as a storage location for the ingested data, a set of data variables from the asset that are ingested, and/or a rate at which data from the asset is ingested.

20 Claims, 8 Drawing Sheets

(58) Field of Classification Search
CPC . G06F 11/3447; G06F 11/3466; G06N 7/005; G05B 23/0205; G05B 23/0264; G05B 23/0283; G05B 23/0286; G05B 23/0297; G06Q 10/063
See application file for complete search history.

(56) References Cited

U.S. PATENT DOCUMENTS

| | | |
|---|---|---|
| 6,256,594 B1 | 7/2001 | Yamamoto et al. |
| 6,336,065 B1 | 1/2002 | Gibson et al. |
| 6,442,542 B1 | 8/2002 | Ramani et al. |
| 6,473,659 B1 | 10/2002 | Shah et al. |
| 6,622,264 B1 | 9/2003 | Bliley et al. |
| 6,634,000 B1 | 10/2003 | Jammu et al. |
| 6,643,600 B2 | 11/2003 | Yanosik et al. |
| 6,650,949 B1 | 11/2003 | Fera et al. |
| 6,725,398 B1 | 4/2004 | Varma et al. |
| 6,760,631 B1 | 7/2004 | Berkowitz et al. |
| 6,775,641 B2 | 8/2004 | Wegerich et al. |
| 6,799,154 B1 | 9/2004 | Aragones et al. |
| 6,823,253 B2 | 11/2004 | Brunell |
| 6,859,739 B2 | 2/2005 | Wegerich et al. |
| 6,892,163 B1 | 5/2005 | Herzog et al. |
| 6,947,797 B2 | 9/2005 | Dean et al. |
| 6,952,662 B2 | 10/2005 | Wegerich et al. |
| 6,957,172 B2 | 10/2005 | Wegerich |
| 6,975,962 B2 | 12/2005 | Wegerich et al. |
| 7,020,595 B1 | 3/2006 | Adibhatla et al. |
| 7,082,379 B1 | 7/2006 | Bickford et al. |
| 7,100,084 B2 | 8/2006 | Unkle et al. |
| 7,107,491 B2 | 9/2006 | Graichen et al. |
| 7,120,685 B2 * | 10/2006 | Ullmann ............. G06F 11/0709 709/224 |
| 7,127,371 B2 | 10/2006 | Duckert et al. |
| 7,233,886 B2 | 6/2007 | Wegerich et al. |
| 7,280,941 B2 | 10/2007 | Bonanni et al. |
| 7,308,385 B2 | 12/2007 | Wegerich et al. |
| 7,373,283 B2 | 5/2008 | Herzog et al. |
| 7,403,869 B2 | 7/2008 | Wegerich et al. |
| 7,409,320 B2 | 8/2008 | Wegerich |
| 7,415,382 B1 | 8/2008 | Bickford et al. |
| 7,428,478 B2 | 9/2008 | Aragones |
| 7,447,666 B2 | 11/2008 | Wang |
| 7,457,693 B2 | 11/2008 | Olsen et al. |
| 7,457,732 B2 | 11/2008 | Aragones et al. |
| 7,509,235 B2 | 3/2009 | Bonissone et al. |
| 7,536,364 B2 | 5/2009 | Subbu et al. |
| 7,539,597 B2 | 5/2009 | Wegerich et al. |
| 7,548,830 B2 | 6/2009 | Goebel et al. |
| 7,634,384 B2 | 12/2009 | Eryurek et al. |
| 7,640,145 B2 | 12/2009 | Wegerich et al. |
| 7,647,131 B1 * | 1/2010 | Sadowski ............ G05B 23/0297 700/108 |
| 7,660,705 B1 | 2/2010 | Meek et al. |
| 7,661,032 B2 * | 2/2010 | Eberbach ............. G06F 11/008 707/686 |
| 7,725,293 B2 | 5/2010 | Bonissone et al. |
| 7,730,364 B2 * | 6/2010 | Chang .................. G06F 11/008 714/47.2 |
| 7,739,096 B2 | 6/2010 | Wegerich et al. |
| 7,756,678 B2 | 7/2010 | Bonissone et al. |
| 7,822,578 B2 | 10/2010 | Kasztenny et al. |
| 7,869,908 B2 | 1/2011 | Walker |
| 7,919,940 B2 | 4/2011 | Miller et al. |
| 7,941,701 B2 | 5/2011 | Wegerich et al. |
| 7,962,240 B2 | 6/2011 | Morrison et al. |
| 8,017,411 B2 * | 9/2011 | Sonderman ............. H01L 22/20 438/14 |
| 8,024,069 B2 | 9/2011 | Miller et al. |
| 8,050,800 B2 | 11/2011 | Miller et al. |
| 8,145,578 B2 | 3/2012 | Pershing et al. |
| 8,229,769 B1 | 7/2012 | Hopkins |
| 8,234,420 B2 | 7/2012 | Lueckenbach et al. |
| 8,239,170 B2 | 8/2012 | Wegerich |
| 8,275,577 B2 | 9/2012 | Herzog |
| 8,285,402 B2 | 10/2012 | Lueckenbach et al. |
| 8,311,774 B2 | 11/2012 | Hines |
| 8,352,216 B2 | 1/2013 | Subbu et al. |
| 8,532,795 B2 | 9/2013 | Adavi et al. |
| 8,533,018 B2 | 9/2013 | Miwa et al. |
| 8,560,165 B2 * | 10/2013 | Salman ............. G05B 23/0283 701/31.5 |
| 8,560,494 B1 | 10/2013 | Downing et al. |
| 8,620,618 B2 | 12/2013 | Eryurek et al. |
| 8,620,853 B2 | 12/2013 | Herzog |
| 8,626,385 B2 | 1/2014 | Humphrey |
| 8,645,276 B2 | 2/2014 | Wong et al. |
| 8,660,980 B2 | 2/2014 | Herzog |
| 8,689,108 B1 | 4/2014 | Duffield et al. |
| 8,700,550 B1 | 4/2014 | Bickford et al. |
| 8,713,467 B1 | 4/2014 | Goldenberg et al. |
| 8,786,605 B1 | 7/2014 | Curtis et al. |
| 8,799,799 B1 | 8/2014 | Cervelli et al. |
| 8,812,960 B1 | 8/2014 | Sun et al. |
| 8,825,840 B2 * | 9/2014 | Chung .................. G06F 21/552 709/224 |
| 8,832,594 B1 | 9/2014 | Thompson et al. |
| 8,850,000 B2 | 9/2014 | Collins et al. |
| 8,862,938 B2 | 10/2014 | Souvannarath |
| 8,868,537 B1 | 10/2014 | Colgrove et al. |
| 8,886,601 B1 | 11/2014 | Landau et al. |
| 8,909,656 B2 | 12/2014 | Kumar et al. |
| 8,917,274 B2 | 12/2014 | Ma et al. |
| 8,918,246 B2 | 12/2014 | Friend |
| 8,924,429 B1 | 12/2014 | Fisher et al. |
| 8,935,201 B1 | 1/2015 | Fisher et al. |
| 8,937,619 B2 | 1/2015 | Sharma et al. |
| 8,938,686 B1 | 1/2015 | Erenrich et al. |
| 9,189,485 B2 * | 11/2015 | Suzuki ............. G05B 23/0264 |
| 9,348,710 B2 * | 5/2016 | Al-Wahabi ............ G06F 11/203 |
| 9,355,010 B2 * | 5/2016 | Gao .................... G06F 11/3447 |
| 9,647,906 B2 * | 5/2017 | Asenjo .................... H04L 43/04 |
| 2002/0091972 A1 | 7/2002 | Harris et al. |
| 2002/0152056 A1 | 10/2002 | Herzog et al. |
| 2003/0055666 A1 | 3/2003 | Roddy et al. |
| 2003/0126258 A1 | 7/2003 | Conkright et al. |
| 2004/0181712 A1 | 9/2004 | Taniguchi et al. |
| 2004/0243636 A1 | 12/2004 | Hasiewicz et al. |
| 2005/0119905 A1 | 6/2005 | Wong et al. |
| 2005/0222747 A1 | 10/2005 | Vhora et al. |
| 2007/0263628 A1 | 11/2007 | Axelsson et al. |
| 2008/0059080 A1 | 3/2008 | Greiner et al. |
| 2008/0059120 A1 | 3/2008 | Xiao et al. |
| 2008/0250265 A1 | 10/2008 | Chang et al. |
| 2009/0070628 A1 * | 3/2009 | Gupta .................. G06F 11/008 714/26 |
| 2010/0141423 A1 | 6/2010 | Lin et al. |
| 2010/0198771 A1 * | 8/2010 | Khalak ................ G05B 23/024 706/52 |
| 2012/0271612 A1 | 10/2012 | Barsoum et al. |
| 2012/0310597 A1 | 12/2012 | Uchiyama et al. |
| 2013/0010610 A1 | 1/2013 | Karthikeyan et al. |
| 2013/0024416 A1 | 1/2013 | Herzog |
| 2013/0080843 A1 | 3/2013 | Stergiou et al. |
| 2013/0283773 A1 | 10/2013 | Hague |
| 2013/0325502 A1 | 12/2013 | Robicsek et al. |
| 2014/0012886 A1 | 1/2014 | Downing et al. |
| 2014/0032132 A1 | 1/2014 | Stratton et al. |
| 2014/0060030 A1 | 3/2014 | Ma et al. |
| 2014/0089035 A1 | 3/2014 | Jericho et al. |
| 2014/0105481 A1 | 4/2014 | Hasselbusch et al. |
| 2014/0121868 A1 | 5/2014 | Zhang et al. |
| 2014/0129688 A1 * | 5/2014 | Asenjo .................... H04L 43/04 709/221 |
| 2014/0169398 A1 | 6/2014 | Arndt et al. |
| 2014/0170617 A1 | 6/2014 | Johnson et al. |
| 2014/0184643 A1 | 7/2014 | Friend |
| 2014/0222355 A1 | 8/2014 | Cheim et al. |
| 2014/0281713 A1 * | 9/2014 | Hampapur ............ G06F 11/079 714/26 |
| 2014/0330600 A1 | 11/2014 | Candas et al. |
| 2014/0330749 A1 | 11/2014 | Candas et al. |
| 2014/0351642 A1 | 11/2014 | Bates et al. |

(56) References Cited

U.S. PATENT DOCUMENTS

| | | | |
|---|---|---|---|
| 2014/0357295 A1 | 12/2014 | Skomra et al. | |
| 2014/0358601 A1 | 12/2014 | Smiley et al. | |
| 2014/0365271 A1* | 12/2014 | Smiley | G06Q 10/0635 |
| | | | 705/7.28 |
| 2015/0046870 A1 | 2/2015 | Goldenberg et al. | |
| 2015/0074469 A1* | 3/2015 | Cher | G06F 11/008 |
| | | | 714/47.2 |
| 2015/0113338 A1* | 4/2015 | Maruyama | G06F 11/3037 |
| | | | 714/48 |
| 2015/0163121 A1* | 6/2015 | Mahaffey | G06F 11/0766 |
| | | | 707/687 |
| 2015/0205657 A1* | 7/2015 | Clark | G06F 11/008 |
| | | | 714/47.3 |
| 2015/0262060 A1 | 9/2015 | Husain et al. | |
| 2016/0261481 A1* | 9/2016 | Ogata | G05B 23/0264 |

FOREIGN PATENT DOCUMENTS

| | | |
|---|---|---|
| WO | 2013034420 | 3/2013 |
| WO | 2014145977 | 9/2014 |
| WO | 2014205497 | 12/2014 |

OTHER PUBLICATIONS

"International Search Report for Application No. PCT/US2016/065262, dated Mar. 20, 2017, 6 pages".
"International Searching Authority, Written Opinion dated Mar. 20, 2017, issued in connection with International Application No. PCT/US2016/065262, filed Dec. 7, 2016, 8 pages."
Biswas, "Redundancy-based Approaches in Wireless Multihop Network Design", PhD Dissertation Submitted to Graduate Faculty of North Carolina State University (2014).
Isermann, "Model-based Fault Detection and Diagnosis—Status and Applications", Institute of Automatic Control, Darmstadt University of Technology (2004).
Narasimhan et al, "Combining Model-Based and Feature-Driven Diagnosis Approaches—A Case Study on Electromechanical Actuators", 21st International Workshop on Principles of Diagnosis (2010).
Prentzas et al, Categorizing Approaches Combining Rule-Based and Case-Based Reasoning.
Infor M3 Enterprise Management System, Infor.com (2014).
Infor Equipment, Infor.com (2012).
Infor Introduces Next-Generation Solution for Equipment Dealers and Service Providers, Infor.com (Feb. 20, 2014).
Infor Equipment for Rental, Infor.com (2013).
Waltermire et al, Applying the Continuous Monitoring Technical Reference Model to the Asset, Configuration, and Vulnerability Management Domains (DRAFT), NIST (Jan. 2012).

* cited by examiner

COMPUTER ARCHITECTURE AND METHOD FOR MODIFYING INTAKE DATA RATE BASED ON A PREDICTIVE MODEL

CROSS REFERENCE TO RELATED APPLICATIONS

This application incorporates by reference the following U.S. patent applications in their entirety: U.S. Non-Provisional patent application Ser. No. 14/732,258, filed on Jun. 5, 2015 and entitled "Asset Health Score." This application also incorporates by reference in their entirety each of the following applications that are being filed on the same day as the present application: U.S. Non-Provisional patent application Ser. No. 14/963,208, entitled "Computer Architecture and Method for Modifying Data Intake Storage Location based on a Predictive Model"; U.S. Non-Provisional patent application Ser. No. 14/963,209, entitled "Computer Architecture and Method for Modifying Intake Data Set based on a Predictive Model"; and U.S. Non-Provisional patent application Ser. No. 14/963,207, entitled "Local Analytics at an Asset."

BACKGROUND

Today, machines (also referred to herein as "assets") are ubiquitous in many industries. From locomotives that transfer cargo across countries to medical equipment that helps nurses and doctors to save lives, assets serve an important role in everyday life. Depending on the role that an asset serves, its complexity, and cost, may vary. For instance, some assets may include multiple subsystems that must operate in harmony for the asset to function properly (e.g., an engine, transmission, etc. of a locomotive).

Because of the key role that assets play in everyday life, it is desirable for assets to be repairable with limited downtime. Accordingly, some have developed mechanisms to monitor and detect abnormal conditions within an asset to facilitate repairing the asset, perhaps with minimal downtime.

OVERVIEW

The current approach for monitoring assets generally involves an on-asset computer that receives operating data in the form of signals from various sensors and/or actuators distributed throughout an asset that monitor the operating conditions of the asset. As one representative example, if the asset is a locomotive, the sensors and/or actuators may monitor parameters such as temperatures, voltages, and speeds, among other examples. If sensor and/or actuator signals from one or more of these devices reach certain values, the on-asset computer may then generate an abnormal-condition indicator, such as a "fault code," which is an indication that an abnormal condition has occurred within the asset.

In general, an abnormal condition may be a defect at an asset or component thereof, which may lead to a failure of the asset and/or component. As such, an abnormal condition may be associated with a given failure, or perhaps multiple failures, in that the abnormal condition is symptomatic of the given failure or failures. In practice, a user typically defines the sensors and respective sensor values associated with each abnormal-condition indicator. That is, the user defines an asset's "normal" operating conditions (e.g., those that do not trigger fault codes) and "abnormal" operating conditions (e.g., those that trigger fault codes).

The on-asset computer may also send sensor signals, actuator signals, and/or abnormal-condition indicator to a remote location such as a remote asset-monitoring system, which may then perform further processing on such data. For instance, a remote asset-monitoring system may use certain data received from an asset as training data for defining a predictive model and/or as input data for executing a predictive model.

In practice, assets may send large volumes of data to a remote asset-monitoring system, but the asset-monitoring system may not necessarily be able to process all of this incoming data. Thus, to reduce the volume of asset data that gets ingested for processing, an asset-monitoring system may be configured to perform a data intake process during which the system may selectively filter, parse, sort, organize, and/or route asset data in accordance with various intake parameters. For example, while an asset may send data streams for a large set of different data variables (e.g., signals from various different sensors/actuators), an asset-monitoring system may be configured to intake only a fixed subset of these data variables. As another example, while an asset may send data streams that are each comprised of a large number of sequential data points for a respective data variable, an asset-monitoring system may be configured to intake data received from the asset in accordance with a fixed intake rate (or "sampling rate"), such that the system intakes only a subset of the data points in each such data stream. Other examples are possible as well. An asset-monitoring system may then route the asset data identified for intake to a predefined storage location where such data can be accessed for further processing, while either discarding or archiving the other asset data.

While this intake process is generally effective at enabling an asset-monitoring system to handle incoming asset data for processing, there may be times when it would be desirable to intake asset data in accordance with modified intake parameters. For instance, if a particular asset appears likely to encounter a failure event in the near future, it may be desirable for an asset-monitoring system to adjust its intake parameters so as to treat data from that asset with a higher level of importance, because such data may generally provide better insight into the cause of a failure event and may thus be more valuable to the process of training a predictive failure model (among other reasons).

The example systems, devices, and methods disclosed herein seek to help address one or more of these issues. In example implementations, a network configuration may include a communication network that facilitates communications between assets and a remote computing system. In some cases, the communication network may facilitate secure communications between assets and the remote computing system (e.g., via encryption or other security measures).

As noted above, each asset may include multiple sensors and/or actuators distributed throughout the asset that facilitate monitoring operating conditions of the asset. A number of assets may provide respective data indicative of each asset's operating conditions to the remote computing system, which may be configured to perform one or more actions based on the provided data.

In example implementations, the remote computing system may be configured to define one or more predictive models that are related to the operation of the assets and then operate in accordance with the one or more predictive models. In general, each such predictive model may receive as inputs sensor data from a particular asset and output a likelihood that at least one event of a given group of events will occur at the asset within a particular period of time in the future. (For purposes of this disclosure, it should be understood that a "group of events" may include either a single event or a plurality of events). As one particular example, the predictive model may output a likelihood that at least one failure even will occur at an asset within a particular period of time in the future. Such a model may be referred to herein as a "failure model." As another example, the predictive models may predict the likelihood that an asset will complete a task within a particular period of time in the future. Other examples of predictive models for an asset may exist as well.

In practice, the predictive model may be defined based on historical data for one or more assets. At a minimum, this historical data may include operating data that indicates operating conditions of a given asset, such as abnormal-condition data identifying instances when failures occurred at assets and/or sensor data indicating one or more physical properties measured at the assets at the time of those instances. The historical data may also include environment data indicating environments in which assets have been operated and scheduling data indicating dates and times when assets were utilized, among other examples of asset-related data used to define the aggregate model-workflow pair.

The one or more predictive models defined by the remote computing system may also correspond to one or more workflows that may be carried out by the remote computing system and/or another entity. In general, a workflow may involve one or more actions that may be performed based on the output of a corresponding model. That is, the output of a given predictive model may cause the remote computing system (or another entity) to perform a corresponding workflow. For instance, a given model-workflow pair may be defined such that when the predictive model outputs a probability that satisfies a given threshold condition, the remote computing system (or another entity) may execute a particular workflow.

In accordance with the present disclosure, a workflow may take the form of one or more actions for adjusting the remote computing system's intake process based on the output of a predictive model. Such an intake workflow may take various forms.

According to one embodiment, an intake workflow may involve modifying the storage location of data ingested from a given asset (or group of assets) based on a predictive model. For example, such a workflow may be configured to route data ingested from a given asset (or group of assets) to a more durable, reliable, and/or robust storage location when a predictive model indicates that at least one event from a given group of events is threshold likely to occur at the given asset (or group of assets) within a particular period of time in the future. Other examples are possible as well.

According to another embodiment, an intake workflow may involve modifying the set of data variables ingested from a given asset (or group of assets) based on a predictive model. For example, such a workflow may be configured to expand the set of data variables ingested from a given asset (or group of assets) to include other data variables when a predictive model indicates that at least one event from a given group of events is threshold likely to occur at the given asset (or group of assets) within a particular period of time in the future. Other examples are possible as well.

According to yet another embodiment, an intake workflow may involve modifying the data ingestion rate for a given asset (or group of assets) based on a predictive model. For example, such a workflow may be configured to increase the rate at which data is ingested from a given asset (or group of assets) when a predictive model indicates that at least one event from a given group of events is threshold likely to occur at the given asset (or group of assets) within a particular period of time in the future. Other examples are possible as well.

It should be understood that two or more of these modification actions may also be combined into a single intake workflow. Further, it should be understood that an intake workflow may involve other actions for adjusting the remote computing system's intake process as well.

Accordingly, in one aspect, disclosed herein is a method for modifying the data ingestion rate for an asset that comprises a computing system (a) operating in a first mode in which the computing system ingests operating data received from a given asset of a plurality of assets at a first ingestion rate, (b) while operating in the first mode, (i) receiving operating data from the given asset, (ii) ingesting at least a portion of the received operating data at the first ingestion rate, and (iii) based on at least a portion of the ingested data, executing a predictive model that outputs an indicator of whether at least one event from a group of events is likely to occur at the given asset within a given period of time in the future, (c) making a determination that the indicator satisfies a threshold condition, (d) in response to the determination, transitioning from operating in the first mode to operating in a second mode in which the computing system ingests operating data from the given asset at a second ingestion rate that differs from the first ingestion rate, and (e) while operating in the second mode, (i) receiving operating data from the given asset and (ii) ingesting at least a portion of the received operating data at the second ingestion rate.

In another aspect, disclosed herein is a computing device that includes (a) a data intake system, (b) at least one processor, (c) a non-transitory computer-readable medium, and (d) program instructions stored on the non-transitory computer-readable medium that are executable by the at least one processor to cause the computing system to carry out functions disclosed herein for modifying the data ingestion rate for an asset.

In yet another aspect, disclosed herein is a non-transitory computer readable medium having instructions stored thereon, where the instructions are executable by a processor to cause a computing system to carry out functions disclosed herein for modifying the data ingestion rate for an asset.

One of ordinary skill in the art will appreciate these as well as numerous other aspects in reading the following disclosure.

DETAILED DESCRIPTION

The following disclosure makes reference to the accompanying figures and several exemplary scenarios. One of ordinary skill in the art will understand that such references are for the purpose of explanation only and are therefore not meant to be limiting. Part or all of the disclosed systems, devices, and methods may be rearranged, combined, added to, and/or removed in a variety of manners, each of which is contemplated herein.

I. EXAMPLE NETWORK CONFIGURATION

Figure 1:
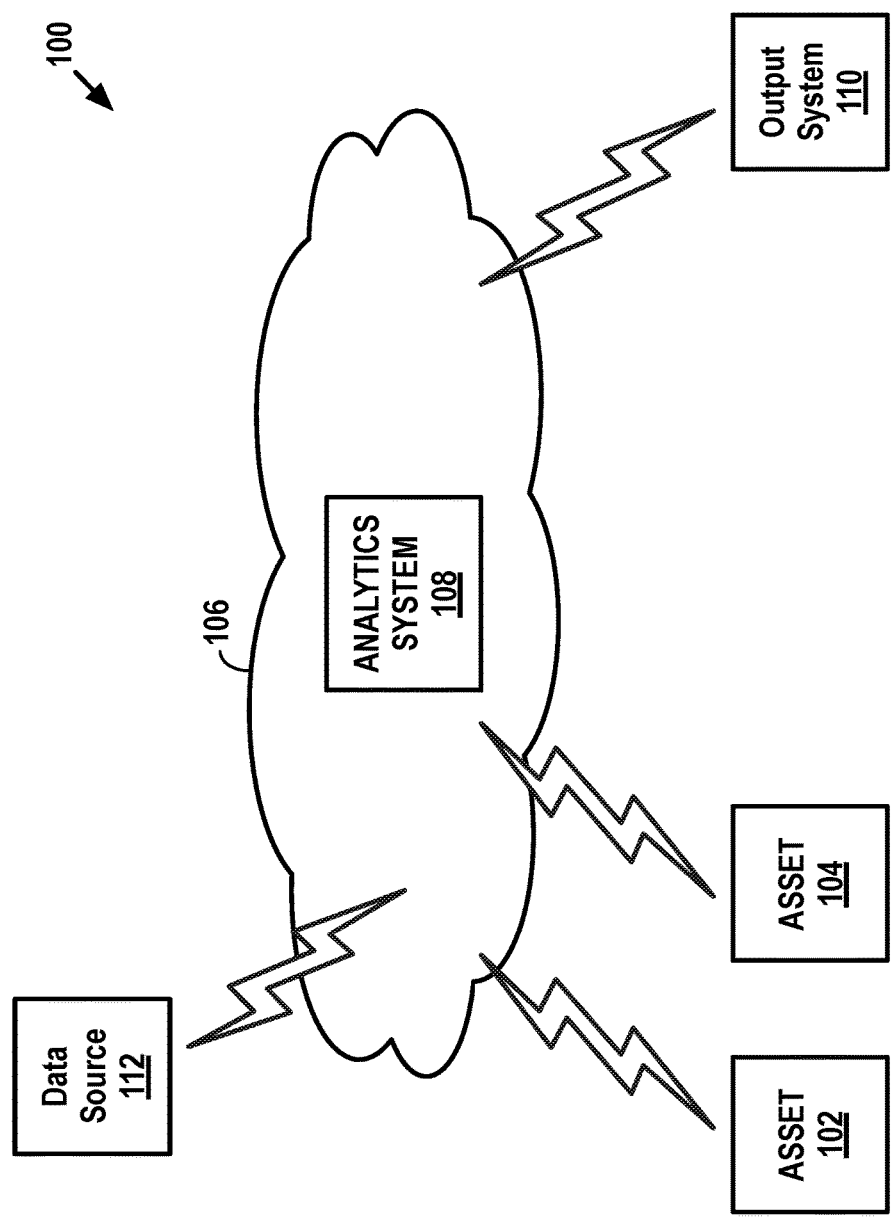
FIG. 1 depicts an example network configuration in which example embodiments may be implemented.

Turning now to the figures, FIG. 1 depicts an example network configuration 100 in which example embodiments may be implemented. As shown, the network configuration 100 includes an asset 102, an asset 104, a communication network 106, a remote computing system 108 that may take the form of an analytics system, an output system 110, and a data source 112.

The communication network 106 may communicatively connect each of the components in the network configuration 100. For instance, the assets 102 and 104 may communicate with the analytics system 108 via the communication network 106. In some cases, the assets 102 and 104 may communicate with one or more intermediary systems, such as an asset gateway (not pictured), that in turn communicates with the analytics system 108. Likewise, the analytics system 108 may communicate with the output system 110 via the communication network 106. In some cases, the analytics system 108 may communicate with one or more intermediary systems, such as a host server (not pictured), that in turn communicates with the output system 110. Many other configurations are also possible. In example cases, the communication network 106 may facilitate secure communications between network components (e.g., via encryption or other security measures).

In general, the assets 102 and 104 may take the form of any device configured to perform one or more operations (which may be defined based on the field) and may also include equipment configured to transmit data indicative of one or more operating conditions of the given asset. In some examples, an asset may include one or more subsystems configured to perform one or more respective operations. In practice, multiple subsystems may operate in parallel or sequentially in order for an asset to operate.

Example assets may include transportation machines (e.g., locomotives, aircraft, passenger vehicles, semi-trailer trucks, ships, etc.), industrial machines (e.g., mining equipment, construction equipment, processing equipment, assembly equipment, etc.), medical machines (e.g., medical imaging equipment, surgical equipment, medical monitoring systems, medical laboratory equipment, etc.), utility machines (e.g., turbines, solar farms, etc.), and unmanned aerial vehicles, among other examples. Those of ordinary skill in the art will appreciate that these are but a few examples of assets and that numerous others are possible and contemplated herein.

In example implementations, the assets 102 and 104 may each be of the same type (e.g., a fleet of locomotives or aircrafts, a group of wind turbines, a pool of milling machines, or a set of magnetic resonance imaining (Mill) machines, among other examples) and perhaps may be of the same class (e.g., same equipment type, brand, and/or model). In other examples, the assets 102 and 104 may differ by type, by brand, by model, etc. For example, assets 102 and 103 may be different pieces of equipment at a job site (e.g., an excavation site) or a production facility, among numerous other examples. The assets are discussed in further detail below with reference to FIG. 2.

As shown, the assets 102 and 104, and perhaps the data source 112, may communicate with the analytics system 108 via the communication network 106. In general, the communication network 106 may include one or more computing systems and network infrastructure configured to facilitate transferring data between network components. The communication network 106 may be or may include one or more Wide-Area Networks (WANs) and/or Local-Area Networks (LANs), which may be wired and/or wireless and support secure communication. In some examples, the communication network 106 may include one or more cellular networks and/or the Internet, among other networks. The communication network 106 may operate according to one or more communication protocols, such as LTE, CDMA, GSM, LPWAN, WiFi, Bluetooth, Ethernet, HTTP/S, TCP, CoAP/DTLS and the like. Although the communication network 106 is shown as a single network, it should be understood that the communication network 106 may include multiple, distinct networks that are themselves communicatively linked. The communication network 106 could take other forms as well.

As noted above, the analytics system 108 may be configured to receive data from the assets 102 and 104 and the data source 112. Broadly speaking, the analytics system 108 may include one or more computing systems, such as servers and databases, configured to receive, process, analyze, and output data. The analytics system 108 may be configured according to a given dataflow technology, such as TPL Dataflow or NiFi, among other examples. The analytics system 108 is discussed in further detail below with reference to FIG. 4.

As shown, the analytics system 108 may be configured to transmit data to the assets 102 and 104 and/or to the output system 110. The particular data transmitted may take various forms and will be described in further detail below.

In general, the output system 110 may take the form of a computing system or device configured to receive data and provide some form of output. The output system 110 may take various forms. In one example, the output system 110 may be or include an output device configured to receive data and provide an audible, visual, and/or tactile output in response to the data. In general, an output device may include one or more input interfaces configured to receive user input, and the output device may be configured to transmit data through the communication network 106 based on such user input. Examples of output devices include tablets, smartphones, laptop computers, other mobile computing devices, desktop computers, smart televisions, and the like.

Another example of the output system 110 may take the form of a work-order system configured to output a request for a mechanic or the like to repair an asset. Yet another example of the output system 110 may take the form of a parts-ordering system configured to place an order for a part of an asset and output a receipt thereof. Numerous other output systems are also possible.

The data source 112 may be configured to communicate with the analytics system 108. In general, the data source 112 may be or include one or more computing systems configured to collect, store, and/or provide to other systems, such as the analytics system 108, data that may be relevant to the functions performed by the analytics system 108. The data source 112 may be configured to generate and/or obtain data independently from the assets 102 and 104. As such, the data provided by the data source 112 may be referred to herein as "external data." The data source 112 may be configured to provide current and/or historical data. In practice, the analytics system 108 may receive data from the data source 112 by "subscribing" to a service provided by the data source. However, the analytics system 108 may receive data from the data source 112 in other manners as well.

Examples of the data source 112 include environment data sources, asset-management data sources, and other data sources. In general, environment data sources provide data indicating some characteristic of the environment in which assets are operated. Examples of environment data sources include weather-data servers, global navigation satellite systems (GNSS) servers, map-data servers, and topography-data servers that provide information regarding natural and artificial features of a given area, among other examples.

In general, asset-management data sources provide data indicating events or statuses of entities (e.g., other assets) that may affect the operation or maintenance of assets (e.g., when and where an asset may operate or receive maintenance). Examples of asset-management data sources include traffic-data servers that provide information regarding air, water, and/or ground traffic, asset-schedule servers that provide information regarding expected routes and/or locations of assets on particular dates and/or at particular times, defect detector systems (also known as "hotbox" detectors) that provide information regarding one or more operating conditions of an asset that passes in proximity to the defect detector system, part-supplier servers that provide information regarding parts that particular suppliers have in stock and prices thereof, and repair-shop servers that provide information regarding repair shop capacity and the like, among other examples.

Examples of other data sources include power-grid servers that provide information regarding electricity consumption and external databases that store historical operating data for assets, among other examples. One of ordinary skill in the art will appreciate that these are but a few examples of data sources and that numerous others are possible.

It should be understood that the network configuration 100 is one example of a network in which embodiments described herein may be implemented. Numerous other arrangements are possible and contemplated herein. For instance, other network configurations may include additional components not pictured and/or more or less of the pictured components.

II. EXAMPLE ASSET

Figure 2:
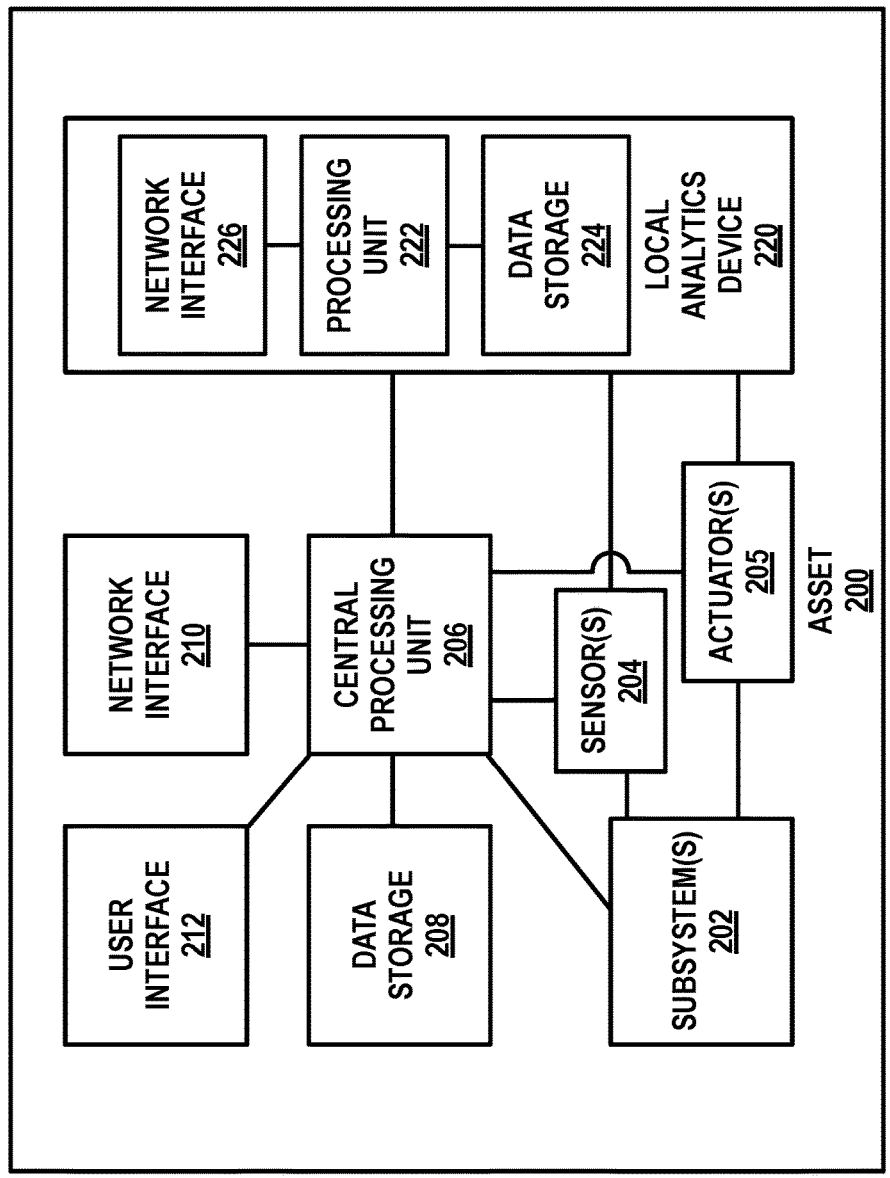
FIG. 2 depicts a simplified block diagram of an example asset.

Turning to FIG. 2, a simplified block diagram of an example asset 200 is depicted. Either or both of assets 102 and 104 from FIG. 1 may be configured like the asset 200. As shown, the asset 200 may include one or more subsystems 202, one or more sensors 204, one or more actuators 205, a central processing unit 206, data storage 208, a network interface 210, a user interface 212, and perhaps also a local analytics device 220, all of which may be communicatively linked (either directly or indirectly) by a system bus, network, or other connection mechanism. One of ordinary skill in the art will appreciate that the asset 200 may include additional components not shown and/or more or less of the depicted components.

Broadly speaking, the asset 200 may include one or more electrical, mechanical, and/or electromechanical components configured to perform one or more operations. In some cases, one or more components may be grouped into a given subsystem 202.

Generally, a subsystem 202 may include a group of related components that are part of the asset 200. A single subsystem 202 may independently perform one or more operations or the single subsystem 202 may operate along with one or more other subsystems to perform one or more operations. Typically, different types of assets, and even different classes of the same type of assets, may include different subsystems.

For instance, in the context of transportation assets, examples of subsystems 202 may include engines, transmissions, drivetrains, fuel systems, battery systems, exhaust systems, braking systems, electrical systems, signal processing systems, generators, gear boxes, rotors, and hydraulic systems, among numerous other subsystems. In the context of a medical machine, examples of subsystems 202 may include scanning systems, motors, coil and/or magnet systems, signal processing systems, rotors, and electrical systems, among numerous other subsystems.

As suggested above, the asset 200 may be outfitted with various sensors 204 that are configured to monitor operating conditions of the asset 200 and various actuators 205 that are configured to interact with the asset 200 or a component thereof and monitor operating conditions of the asset 200. In some cases, some of the sensors 204 and/or actuators 205 may be grouped based on a particular subsystem 202. In this way, the group of sensors 204 and/or actuators 205 may be configured to monitor operating conditions of the particular subsystem 202, and the actuators from that group may be configured to interact with the particular subsystem 202 in some way that may alter the subsystem's behavior based on those operating conditions.

In general, a sensor 204 may be configured to detect a physical property, which may be indicative of one or more operating conditions of the asset 200, and provide an indication, such as an electrical signal, of the detected physical property. In operation, the sensors 204 may be configured to obtain measurements continuously, periodically (e.g., based on a sampling frequency), and/or in response to some triggering event. In some examples, the sensors 204 may be preconfigured with operating parameters for performing measurements and/or may perform measurements in accordance with operating parameters provided by the central processing unit 206 (e.g., sampling signals that instruct the sensors 204 to obtain measurements). In examples, different sensors 204 may have different operating parameters (e.g., some sensors may sample based on a first frequency, while other sensors sample based on a second, different frequency). In any event, the sensors 204 may be configured to transmit electrical signals indicative of a measured physical property to the central processing unit 206. The sensors 204 may continuously or periodically provide such signals to the central processing unit 206.

For instance, sensors 204 may be configured to measure physical properties such as the location and/or movement of the asset 200, in which case the sensors may take the form of GNSS sensors, dead-reckoning-based sensors, accelerometers, gyroscopes, pedometers, magnetometers, or the like.

Additionally, various sensors 204 may be configured to measure other operating conditions of the asset 200, examples of which may include temperatures, pressures, speeds, acceleration or deceleration rates, friction, power usages, fuel usages, fluid levels, runtimes, voltages and currents, magnetic fields, electric fields, presence or absence of objects, positions of components, and power generation, among other examples. One of ordinary skill in the art will appreciate that these are but a few example operating conditions that sensors may be configured to measure. Additional or fewer sensors may be used depending on the industrial application or specific asset.

As suggested above, an actuator 205 may be configured similar in some respects to a sensor 204. Specifically, an actuator 205 may be configured to detect a physical property indicative of an operating condition of the asset 200 and provide an indication thereof in a manner similar to the sensor 204.

Moreover, an actuator 205 may be configured to interact with the asset 200, one or more subsystems 202, and/or some component thereof. As such, an actuator 205 may include a motor or the like that is configured to perform a mechanical operation (e.g., move) or otherwise control a component, subsystem, or system. In a particular example, an actuator may be configured to measure a fuel flow and alter the fuel flow (e.g., restrict the fuel flow), or an actuator may be configured to measure a hydraulic pressure and alter the hydraulic pressure (e.g., increase or decrease the hydraulic pressure). Numerous other example interactions of an actuator are also possible and contemplated herein.

Generally, the central processing unit 206 may include one or more processors and/or controllers, which may take the form of a general- or special-purpose processor or controller. In particular, in example implementations, the central processing unit 206 may be or include microprocessors, microcontrollers, application specific integrated circuits, digital signal processors, and the like. In turn, the data storage 208 may be or include one or more non-transitory computer-readable storage media, such as optical, magnetic, organic, or flash memory, among other examples.

The central processing unit 206 may be configured to store, access, and execute computer-readable program instructions stored in the data storage 208 to perform the operations of an asset described herein. For instance, as suggested above, the central processing unit 206 may be configured to receive respective sensor signals from the sensors 204 and/or actuators 205. The central processing unit 206 may be configured to store sensor and/or actuator data in and later access it from the data storage 208.

The central processing unit 206 may also be configured to determine whether received sensor and/or actuator signals trigger any abnormal-condition indicators, such as fault codes. For instance, the central processing unit 206 may be configured to store in the data storage 208 abnormal-condition rules, each of which include a given abnormal-condition indicator representing a particular abnormal condition and respective triggering criteria that trigger the abnormal-condition indicator. That is, each abnormal-condition indicator corresponds with one or more sensor and/or actuator measurement values that must be satisfied before the abnormal-condition indicator is triggered. In practice, the asset 200 may be pre-programmed with the abnormal-condition rules and/or may receive new abnormal-condition rules or updates to existing rules from a computing system, such as the analytics system 108.

In any event, the central processing unit 206 may be configured to determine whether received sensor and/or actuator signals trigger any abnormal-condition indicators. That is, the central processing unit 206 may determine whether received sensor and/or actuator signals satisfy any triggering criteria. When such a determination is affirmative, the central processing unit 206 may generate abnormal-condition data and then may also cause the asset's network interface 210 to transmit the abnormal-condition data to the analytics system 108 and/or cause the asset's user interface 212 to output an indication of the abnormal condition, such as a visual and/or audible alert. Additionally, the central processing unit 206 may log the occurrence of the abnormal-condition indicator being triggered in the data storage 208, perhaps with a timestamp.

Figure 3:
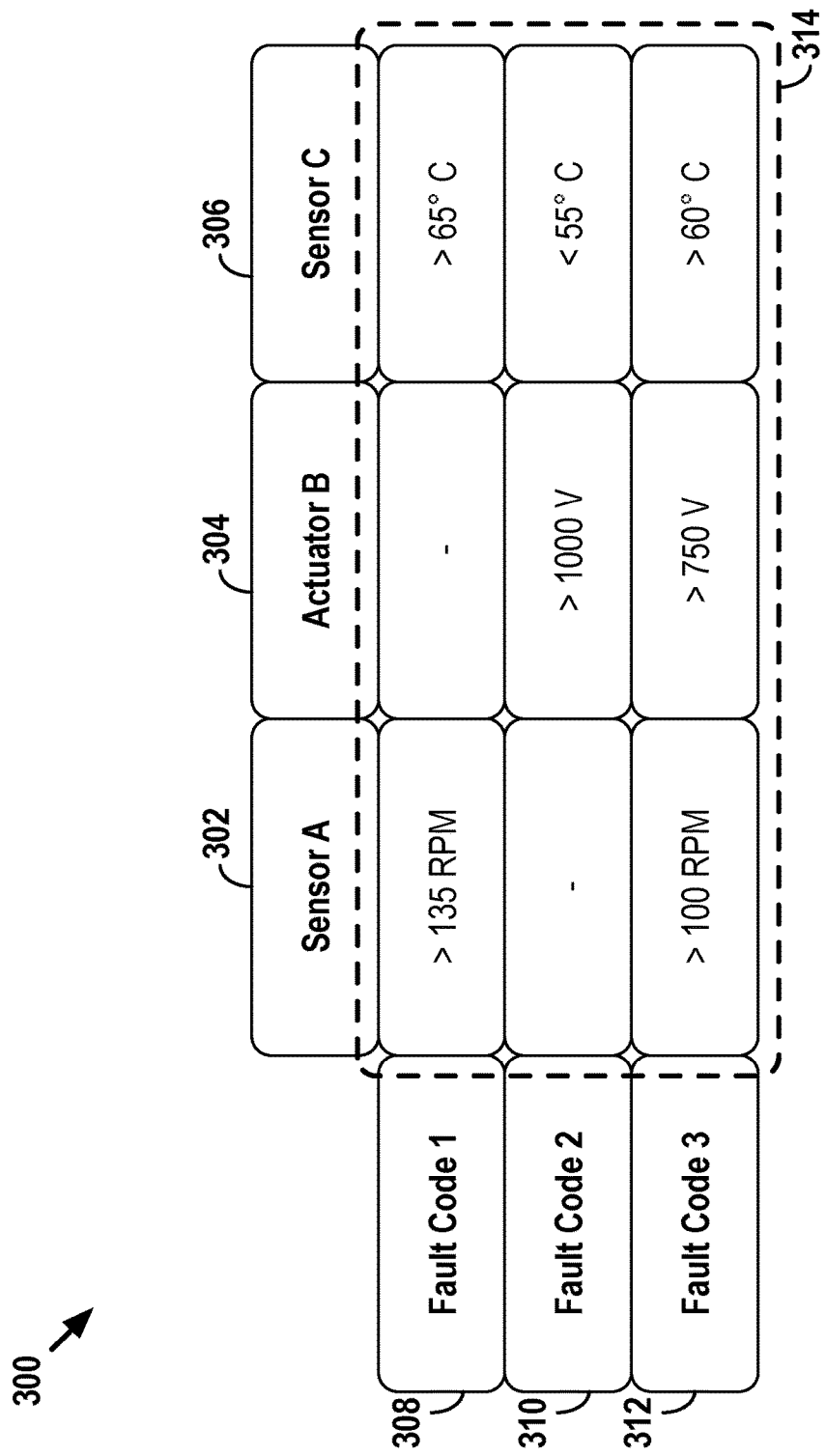
FIG. 3 depicts a conceptual illustration of example abnormal-condition indicators and triggering criteria.

FIG. 3 depicts a conceptual illustration of example abnormal-condition indicators and respective triggering criteria for an asset. In particular, FIG. 3 depicts a conceptual illustration of example fault codes. As shown, table 300 includes columns 302, 304, and 306 that correspond to Sensor A, Actuator B, and Sensor C, respectively, and rows 308, 310, and 312 that correspond to Fault Codes 1, 2, and 3, respectively. Entries 314 then specify sensor criteria (e.g., sensor value thresholds) that correspond to the given fault codes.

For example, Fault Code 1 will be triggered when Sensor A detects a rotational measurement greater than 135 revolutions per minute (RPM) and Sensor C detects a temperature measurement greater than 65° Celsius (C), Fault Code 2 will be triggered when Actuator B detects a voltage measurement greater than 1000 Volts (V) and Sensor C detects a temperature measurement less than 55° C., and Fault Code 3 will be triggered when Sensor A detects a rotational measurement greater than 100 RPM, Actuator B detects a voltage measurement greater than 750 V, and Sensor C detects a temperature measurement greater than 60° C. One of ordinary skill in the art will appreciate that FIG. 3 is provided for purposes of example and explanation only and that numerous other fault codes and/or triggering criteria are possible and contemplated herein.

Referring back to FIG. 2, the central processing unit 206 may be configured to carry out various additional functions for managing and/or controlling operations of the asset 200 as well. For example, the central processing unit 206 may be configured to provide instruction signals to the subsystems 202 and/or the actuators 205 that cause the subsystems 202 and/or the actuators 205 to perform some operation, such as modifying a throttle position. Additionally, the central processing unit 206 may be configured to modify the rate at which it processes data from the sensors 204 and/or the actuators 205, or the central processing unit 206 may be configured to provide instruction signals to the sensors 204 and/or actuators 205 that cause the sensors 204 and/or actuators 205 to, for example, modify a sampling rate. Moreover, the central processing unit 206 may be configured to receive signals from the subsystems 202, the sensors 204, the actuators 205, the network interfaces 210, and/or the user interfaces 212 and based on such signals, cause an operation to occur. Further still, the central processing unit 206 may be configured to receive signals from a computing device, such as a diagnostic device, that cause the central processing unit 206 to execute one or more diagnostic tools in accordance with diagnostic rules stored in the data storage 208. Other functionalities of the central processing unit 206 are discussed below.

The network interface 210 may be configured to provide for communication between the asset 200 and various network components connected to communication network 106. For example, the network interface 210 may be configured to facilitate wireless communications to and from the communication network 106 and may thus take the form of an antenna structure and associated equipment for transmitting and receiving various over-the-air signals. Other examples are possible as well. In practice, the network interface 210 may be configured according to a communication protocol, such as but not limited to any of those described above.

The user interface 212 may be configured to facilitate user interaction with the asset 200 and may also be configured to facilitate causing the asset 200 to perform an operation in response to user interaction. Examples of user interfaces 212 include touch-sensitive interfaces, mechanical interfaces (e.g., levers, buttons, wheels, dials, keyboards, etc.), and other input interfaces (e.g., microphones), among other examples. In some cases, the user interface 212 may include or provide connectivity to output components, such as display screens, speakers, headphone jacks, and the like.

The local analytics device 220 may generally be configured to receive and analyze data related to the asset 200 and based on such analysis, may cause one or more operations to occur at the asset 200. For instance, the local analytics device 220 may receive operating data for the asset 200 (e.g., data generated by the sensors 204 and/or actuators 205) and based on such data, may provide instructions to the central processing unit 206, the sensors 204, and/or the actuators 205 that cause the asset 200 to perform an operation.

To facilitate this operation, the local analytics device 220 may include one or more asset interfaces that are configured to couple the local analytics device 220 to one or more of the asset's on-board systems. For instance, as shown in FIG. 2, the local analytics device 220 may have an interface to the asset's central processing unit 206, which may enable the local analytics device 220 to receive operating data from the central processing unit 206 (e.g., operating data that is generated by sensors 204 and/or actuators 205 and sent to the central processing unit 206) and then provide instructions to the central processing unit 206. In this way, the local analytics device 220 may indirectly interface with and receive data from other on-board systems of the asset 200 (e.g., the sensors 204 and/or actuators 205) via the central processing unit 206. Additionally or alternatively, as shown in FIG. 2, the local analytics device 220 could have an interface to one or more sensors 204 and/or actuators 205, which may enable the local analytics device 220 to communicate directly with the sensors 204 and/or actuators 205. The local analytics device 220 may interface with the on-board systems of the asset 200 in other manners as well, including the possibility that the interfaces illustrated in FIG. 2 are facilitated by one or more intermediary systems that are not shown.

In practice, the local analytics device 220 may enable the asset 200 to locally perform advanced analytics and associated operations, such as executing a predictive model and corresponding workflow, that may otherwise not be able to be performed with the other on-asset components. As such, the local analytics device 220 may help provide additional processing power and/or intelligence to the asset 200.

It should be understood that the local analytics device 220 may also be configured to cause the asset 200 to perform operations that are not related a predictive model. For example, the local analytics device 220 may receive data from a remote source, such as the analytics system 108 or the output system 110, and based on the received data cause the asset 200 to perform one or more operations. One particular example may involve the local analytics device 220 receiving a firmware update for the asset 200 from a remote source and then causing the asset 200 to update its firmware. Another particular example may involve the local analytics device 220 receiving a diagnosis instruction from a remote source and then causing the asset 200 to execute a local diagnostic tool in accordance with the received instruction. Numerous other examples are also possible.

As shown, in addition to the one or more asset interfaces discussed above, the local analytics device 220 may also include a processing unit 222, a data storage 224, and a network interface 226, all of which may be communicatively linked by a system bus, network, or other connection mechanism. The processing unit 222 may include any of the components discussed above with respect to the central processing unit 206. In turn, the data storage 224 may be or include one or more non-transitory computer-readable storage media, which may take any of the forms of computer-readable storage media discussed above.

The processing unit 222 may be configured to store, access, and execute computer-readable program instructions stored in the data storage 224 to perform the operations of a local analytics device described herein. For instance, the processing unit 222 may be configured to receive respective sensor and/or actuator signals generated by the sensors 204 and/or actuators 205 and may execute a predictive model-workflow pair based on such signals. Other functions are described below.

The network interface 226 may be the same or similar to the network interfaces described above. In practice, the network interface 226 may facilitate communication between the local analytics device 220 and the analytics system 108.

In some example implementations, the local analytics device 220 may include and/or communicate with a user interface that may be similar to the user interface 212. In practice, the user interface may be located remote from the local analytics device 220 (and the asset 200). Other examples are also possible.

While FIG. 2 shows the local analytics device 220 physically and communicatively coupled to its associated asset (e.g., the asset 200) via one or more asset interfaces, it should also be understood that this might not always be the case. For example, in some implementations, the local analytics device 220 may not be physically coupled to its associated asset and instead may be located remote from the asset 220. In an example of such an implementation, the local analytics device 220 may be wirelessly, communicatively coupled to the asset 200. Other arrangements and configurations are also possible.

One of ordinary skill in the art will appreciate that the asset 200 shown in FIG. 2 is but one example of a simplified representation of an asset and that numerous others are also possible. For instance, other assets may include additional components not pictured and/or more or less of the pictured components. Moreover, a given asset may include multiple, individual assets that are operated in concert to perform operations of the given asset. Other examples are also possible.

III. EXAMPLE ANALYTICS SYSTEM

Figure 4:
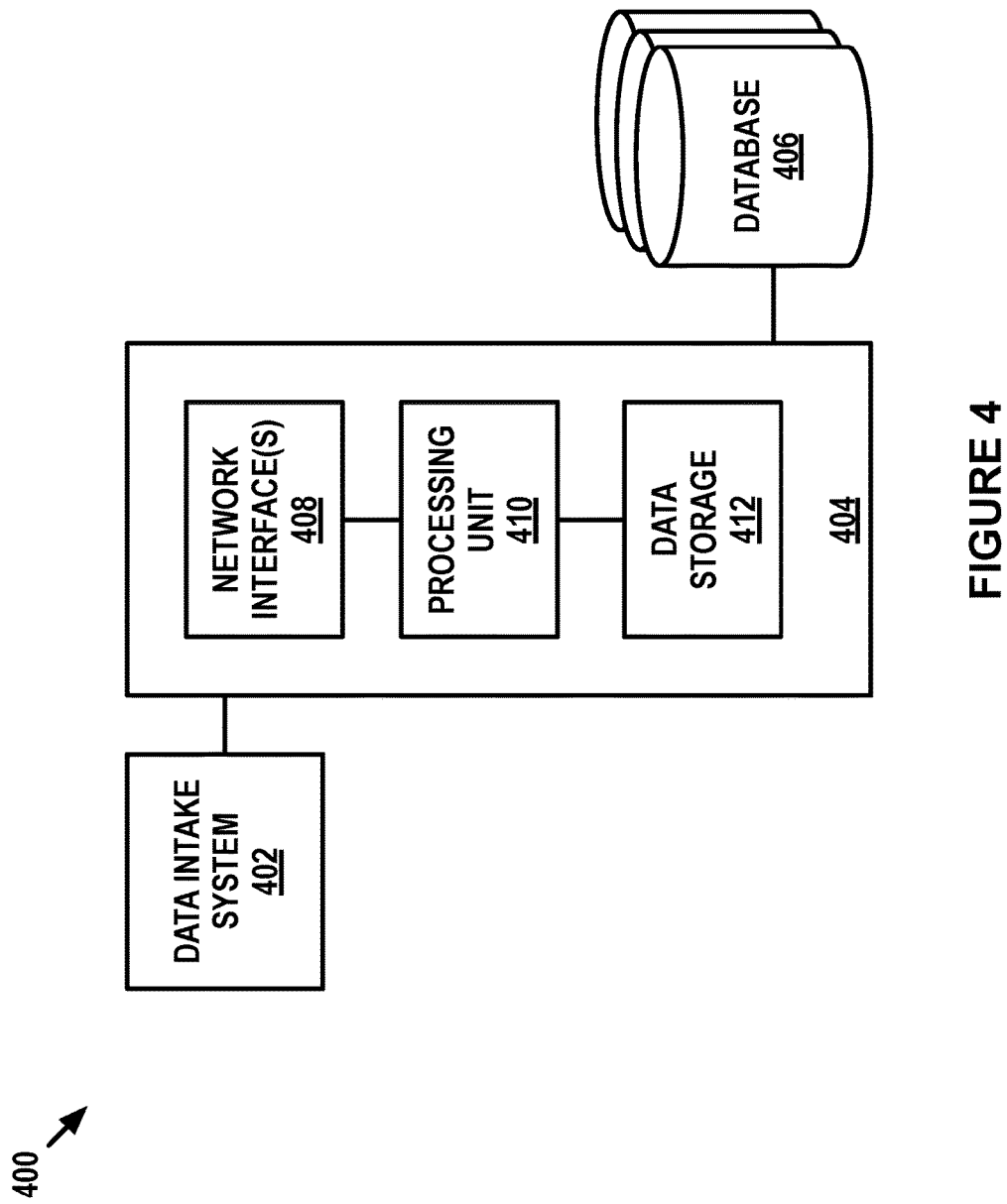
FIG. 4 depicts a simplified block diagram of an example analytics system.

Referring now to FIG. 4, a simplified block diagram of an example analytics system 400 is depicted. As suggested above, the analytics system 400 may include one or more computing systems communicatively linked and arranged to carry out various operations described herein. Specifically, as shown, the analytics system 400 may include a data intake system 402, a data science system 404, and one or more databases 406. These system components may be communicatively coupled via one or more wireless and/or wired connections, which may be configured to facilitate secure communications.

The data intake system 402 may generally function to receive data and then ingest at least a portion of the received data for output to the data science system 404. As such, the data intake system 402 may include one or more network interfaces configured to receive data from various network components of the network configuration 100, such as the assets 102 and 104, the output system 110, and/or the data source 112. Specifically, the data intake system 402 may be configured to receive analog signals, data streams, and/or network packets, among other examples. As such, the network interfaces may include one or more wired network interfaces, such as a port or the like, and/or wireless network interfaces, similar to those described above. In some examples, the data intake system 402 may be or include components configured according to a given dataflow technology, such as a NiFi receiver or the like.

The data intake system 402 may include one or more processing components configured to perform one or more operations. Example operations may include compression and/or decompression, encryption and/or de-encryption, analog-to-digital and/or digital-to-analog conversion, amplification, formatting, and packaging, among other operations. Moreover, the data intake system 402 may be configured to filter, parse, sort, organize, route, and/or store data in accordance with one or more intake parameters, which may be modified in accordance with the present disclosure. For example, the data intake system 402 may operate in accordance with an intake parameter that defines the particular set of data variables to intake from an asset (e.g., the particular set of asset sensor/actuator readings to be ingested). As another example, the data intake system 402 may operate in accordance with an intake parameter that defines a rate at which to intake data from an asset (i.e., a sampling frequency). As yet another example, the data intake system 402 may operate in accordance with an intake parameter that defines a storage location for data ingested from an asset. The data intake system 402 may operate in accordance with other intake parameters as well.

In general, the data received by the data intake system 402 may take various forms. For example, the payload of the data may include a single sensor or actuator measurement, multiple sensor and/or actuator measurements and/or one or more abnormal-condition data. Other examples are also possible.

Moreover, the received data may include certain characteristics, such as a source identifier and a timestamp (e.g., a date and/or time at which the information was obtained). For instance, a unique identifier (e.g., a computer generated alphabetic, numeric, alphanumeric, or the like identifier) may be assigned to each asset, and perhaps to each sensor and actuator. Such identifiers may be operable to identify the asset, sensor, or actuator from which data originates. In some cases, another characteristic may include the location (e.g., GPS coordinates) at which the information was obtained. Data characteristics may come in the form of signal signatures or metadata, among other examples.

The data science system 404 may generally function to receive (e.g., from the data intake system 402) and analyze data and based on such analysis, cause one or more operations to occur. As such, the data science system 404 may include one or more network interfaces 408, a processing unit 410, and data storage 412, all of which may be communicatively linked by a system bus, network, or other connection mechanism. In some cases, the data science system 404 may be configured to store and/or access one or more application program interfaces (APIs) that facilitate carrying out some of the functionality disclosed herein.

The network interfaces 408 may be the same or similar to any network interface described above. In practice, the network interfaces 408 may facilitate communication (e.g., with some level of security) between the data science system 404 and various other entities, such as the data intake system 402, the databases 406, the assets 102, the output system 110, etc.

The processing unit 410 may include one or more processors, which may take any of the processor forms described above. In turn, the data storage 412 may be or include one or more non-transitory computer-readable storage media, which may take any of the forms of computer-readable storage media discussed above. The processing unit 410 may be configured to store, access, and execute computer-readable program instructions stored in the data storage 412 to perform the operations of an analytics system described herein.

In general, the processing unit 410 may be configured to perform analytics on data received from the data intake system 402. To that end, the processing unit 410 may be configured to execute one or more modules, which may each take the form of one or more sets of program instructions that are stored in the data storage 412. The modules may be configured to facilitate causing an outcome to occur based on the execution of the respective program instructions. An example outcome from a given module may include outputting data into another module, updating the program instructions of the given module and/or of another module, and outputting data to a network interface 408 for transmission to an asset and/or the output system 110, among other examples.

The databases 406 may generally function to receive (e.g., from the data science system 404) and store data. As such, each database 406 may include one or more non-transitory computer-readable storage media, such as any of the examples provided above. In practice, the databases 406 may be separate from or integrated with the data storage 412.

The databases 406 may be configured to store numerous types of data, some of which is discussed below. In practice, some of the data stored in the databases 406 may include a timestamp indicating a date and time at which the data was generated or added to the database. Moreover, data may be stored in a number of manners in the databases 406. For instance, data may be stored in time sequence, in a tabular manner, and/or organized based on data source type (e.g., based on asset, asset type, sensor, sensor type, actuator, or actuator type) or abnormal-condition indicator, among other examples. In accordance with the present disclosure, the databases may also have different storage characteristics, such as different levels of durability, accessibility and/or reliability. Representative examples of database types may include time-series databases, document databases, relational databases, and graph databases, among others.

IV. EXAMPLE OPERATIONS

The operations of the example network configuration 100 depicted in FIG. 1 will now be discussed in further detail below. To help describe some of these operations, flow diagrams may be referenced to describe combinations of operations that may be performed. In some cases, each block may represent a module or portion of program code that includes instructions that are executable by a processor to implement specific logical functions or steps in a process. The program code may be stored on any type of computer-readable medium, such as non-transitory computer-readable media. In other cases, each block may represent circuitry that is wired to perform specific logical functions or steps in a process. Moreover, the blocks shown in the flow diagrams may be rearranged into different orders, combined into fewer blocks, separated into additional blocks, and/or removed based upon the particular embodiment.

The following description may reference examples where a single data source, such as the asset 102, provides data to the analytics system 108 that then performs one or more functions. It should be understood that this is done merely for sake of clarity and explanation and is not meant to be limiting. In practice, the analytics system 108 generally receives data from multiple sources, perhaps simultaneously, and performs operations based on such aggregate received data.

A. Collection of Operating Data

As mentioned above, the representative asset 102 may take various forms and may be configured to perform a number of operations. In a non-limiting example, the asset 102 may take the form of a locomotive that is operable to transfer cargo across the United States. While in transit, the sensors and/or actuators of the asset 102 may obtain data that reflects one or more operating conditions of the asset 102. The sensors and/or actuators may transmit the data to a processing unit of the asset 102.

The processing unit may be configured to receive the data from the sensors and/or actuators. In practice, the processing unit may receive sensor data from multiple sensors and/or actuator data from multiple actuators simultaneously or sequentially. As discussed above, while receiving this data, the processing unit may also be configured to determine whether the data satisfies triggering criteria that trigger any abnormal-condition indicators, such as fault codes. In the event the processing unit determines that one or more abnormal-condition indicators are triggered, the processing unit may be configured to perform one or more local operations, such as outputting an indication of the triggered indicator via a user interface.

The asset 102 may then transmit operating data to the analytics system 108 via a network interface of the asset 102 and the communication network 106. In operation, the asset 102 may transmit operating data to the analytics system 108 continuously, periodically, and/or in response to triggering events (e.g., abnormal conditions). Specifically, the asset 102 may transmit operating data periodically based on a particular frequency (e.g., daily, hourly, every fifteen minutes, once per minute, once per second, etc.), or the asset 102 may be configured to transmit a continuous, real-time feed of operating data. Additionally or alternatively, the asset 102 may be configured to transmit operating data based on certain triggers, such as when sensor and/or actuator measurements satisfy triggering criteria for any abnormal-condition indicators. The asset 102 may transmit operating data in other manners as well.

In practice, operating data for the asset 102 may include sensor data, actuator data, abnormal-condition data, and/or other asset event data (e.g., data indicating asset shutdowns, restarts, etc.). In some implementations, the asset 102 may be configured to provide the operating data in a single data stream, while in other implementations the asset 102 may be configured to provide the operating data in multiple, distinct data streams. For example, the asset 102 may provide to the analytics system 108 a first data stream of sensor and/or actuator data and a second data stream of abnormal-condition data. As another example, the asset 102 may provide to the analytics system 108 a separate data stream for each respective sensor and/or actuator on the asset 102. Other possibilities also exist.

Sensor and actuator data may take various forms. For example, at times, sensor data (or actuator data) may include measurements obtained by each of the sensors (or actuators) of the asset 102. While at other times, sensor data (or actuator data) may include measurements obtained by a subset of the sensors (or actuators) of the asset 102.

Specifically, the sensor and/or actuator data may include measurements obtained by the sensors and/or actuators associated with a given triggered abnormal-condition indicator. For example, if a triggered fault code is Fault Code 1 from FIG. 3, then sensor data may include raw measurements obtained by Sensors A and C. Additionally or alternatively, the data may include measurements obtained by one or more sensors or actuators not directly associated with the triggered fault code. Continuing off the last example, the data may additionally include measurements obtained by Actuator B and/or other sensors or actuators. In some examples, the asset 102 may include particular sensor data in the operating data based on a fault-code rule or instruction provided by the analytics system 108, which may have, for example, determined that there is a correlation between that which Actuator B is measuring and that which caused the Fault Code 1 to be triggered in the first place. Other examples are also possible.

Further still, the data may include one or more sensor and/or actuator measurements from each sensor and/or actuator of interest based on a particular time of interest, which may be selected based on a number of factors. In some examples, the particular time of interest may be based on a sampling rate. In other examples, the particular time of interest may be based on the time at which an abnormal-condition indicator is triggered.

In particular, based on the time at which an abnormal-condition indicator is triggered, the data may include one or more respective sensor and/or actuator measurements from each sensor and/or actuator of interest (e.g., sensors and/or actuators directly and indirectly associated with the triggered indicator). The one or more measurements may be based on a particular number of measurements or particular duration of time around the time of the triggered abnormal-condition indicator.

For example, if a triggered fault code is Fault Code 2 from FIG. 3, the sensors and actuators of interest might include Actuator B and Sensor C. The one or more measurements may include the most recent respective measurements obtained by Actuator B and Sensor C prior to the triggering of the fault code (e.g., triggering measurements) or a respective set of measurements before, after, or about the triggering measurements. For example, a set of five measurements may include the five measurements before or after the triggering measurement (e.g., excluding the triggering measurement), the four measurements before or after the triggering measurement and the triggering measurement, or the two measurements before and the two after as well as the triggering measurement, among other possibilities.

Similar to sensor and actuator data, the abnormal-condition data may take various forms. In general, the abnormal-condition data may include or take the form of an indicator that is operable to uniquely identify a particular abnormal condition that occurred at the asset 102 from all other abnormal conditions that may occur at the asset 102. The abnormal-condition indicator may take the form of an alphabetic, numeric, or alphanumeric identifier, among other examples. Moreover, the abnormal-condition indicator may take the form of a string of words that is descriptive of the abnormal condition, such as "Overheated Engine" or "Out of Fuel", among other examples.

The analytics system 108, and in particular, the data intake system of the analytics system 108, may be configured to receive operating data from one or more assets and/or data sources. The data intake system may be configured to intake at least a portion of the received data, perform one or more operations to the received data, and then relay the data to the data science system of the analytics system 108. In turn, the data science system may analyze the received data and based on such analysis, perform one or more operations.

B. Defining Predictive Models & Workflows

As one example, the analytics system 108 may be configured to define predictive models and corresponding workflows based on received operating data for one or more assets and/or received external data related to the one or more assets. The analytics system 108 may define model-workflow pairs based on various other data as well.

In general, a model-workflow pair may include a set of program instructions that cause an asset to monitor certain operating conditions in order to determine the likelihood that at least one event of a given group of events will occur in the future and then carry out certain operations if this likelihood reaches a threshold. For instance, a predictive model may include one or more algorithms whose inputs are sensor and/or actuator data from one or more sensors and/or actuators of an asset and whose outputs are utilized to determine a probability that a particular type of event may occur (or that no such event may occur) at the asset within a particular period of time in the future. In turn, a workflow may include one or more triggers (e.g., model output values) and corresponding operations that the asset carries out based on the triggers.

In practice, the analytics system 108 may be configured to define aggregate and/or individualized predictive models and/or workflows. An "aggregate" model/workflow may refer to a model/workflow that is generic for a group of assets and defined without taking into consideration particular characteristics of the assets. On the other hand, an "individualized" model/workflow may refer to a model/workflow that is specifically tailored for a single asset or a subgroup of assets from the group of assets and defined based on particular characteristics of the single asset or subgroup of assets.

According to the present disclosure, one implementation of a model-workflow pair may take the form of a model for predicting the likelihood of at least one event of a given group of events occurring at an asset within a particular period of time in the future (e.g., within a certain number of hours, days, or weeks in the future) and a corresponding workflow for adjusting the analytics system's intake process based on this predictive model. This model-workflow pair may take various forms.

1. Predictive Model for Adjusting Intake Operation

As noted above, the analytics system 108 may be configured to define a model for predicting the likelihood of at least one event of a given group of events occurring at the asset within a particular period of time in the future. In practice, the group of events may be defined to include any event that may impact the analytics system's desire to adjust its intake process. Examples of such events may include an asset failure, an asset restart, an asset shutdown, and/or the occurrence of an abnormal condition at the asset (e.g., an anomaly in a sensor/actuator value or combination of sensor/actuator values). The analytics system 108 may define such a predictive model in various manners.

Figure 5:
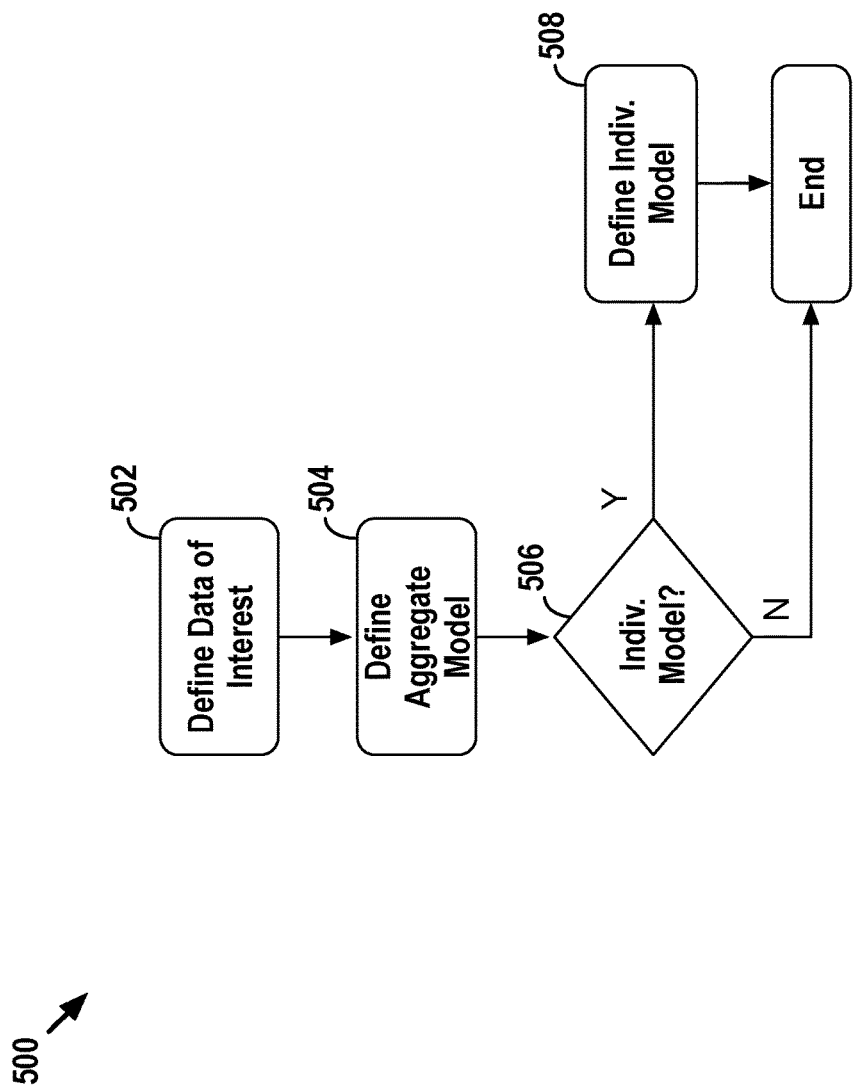
FIG. 5 depicts an example flow diagram of a definition phase that may be used for defining a predictive model.

FIG. 5 is a flow diagram 500 depicting one possible example of a definition phase that may be used for defining model-workflow pairs. For purposes of illustration, the example definition phase is described as being carried out by the analytics system 108, but this definition phase may be carried out by other systems as well. One of ordinary skill in the art will appreciate that the flow diagram 500 is provided for sake of clarity and explanation and that numerous other combinations of operations may be utilized to define a predictive model.

As shown in FIG. 5, at block 502, the analytics system 108 may begin by defining a set of data that forms the basis for a given predictive model (e.g., the data of interest). The data of interest may derive from a number of sources, such as the assets 102 and 104 and the data source 112, and may be stored in a database of the analytics system 108.

The data of interest may include historical data for a particular set of assets from a group of assets or all of the assets from a group of assets (e.g., the assets of interest). Moreover, the data of interest may include measurements from a particular set of sensors and/or actuators from each of the assets of interest or from all of the sensors and/or actuators from each of the assets of interest. Further still, the data of interest may include data from a particular period of time in the past, such as two week's worth of historical data.

The data of interest may include a variety of types data, which may depend on the given predictive model. In some instances, the data of interest may include at least operating data indicating operating conditions of assets, where the operating data is as discussed above in the Collection of Operating Data section. Additionally, the data of interest may include environment data indicating environments in which assets are typically operated and/or scheduling data indicating planned dates and times during which assets are to carry out certain tasks. Other types of data may also be included in the data of interest.

In practice, the data of interest may be defined in a number of manners. In one example, the data of interest may be user-defined. In particular, a user may operate an output system 110 that receives user inputs indicating a selection of certain data of interest, and the output system 110 may provide to the analytics system 108 data indicating such selections. Based on the received data, the analytics system 108 may then define the data of interest.

In another example, the data of interest may be machine-defined. In particular, the analytics system 108 may perform various operations, such as simulations, to determine the data of interest that generates the most accurate predictive model. Other examples are also possible.

Returning to FIG. 5, at block 504, the analytics system 108 may be configured to, based on the data of interest, define an aggregate, predictive model that is related to the operation of assets. In general, an aggregate, predictive model may define a relationship between operating conditions of assets and a likelihood of an occurring at the asset. Specifically, an aggregate, predictive model may receive as inputs sensor data from sensors of an asset and/or actuator data from actuators of the asset and output a probability that at least one event of a given group of events will occur at the asset within a certain amount of time into the future.

As noted above, the group of events may be defined to include any event that may have impact the analytics system's desire to adjust its intake process. These events may vary depending on the particular implementation. For example, such an event may take the form of a failure event that may occur at an asset, in which case the predictive model may predict the likelihood that a failure event will occur within a certain period of time in the future. In another example, such an event may take the form of an action that may be taken by an asset (e.g., a restart or shutdown action), in which case the predictive model may predict the likelihood that an asset will take and/or complete the action within a certain period of time in the future. In yet another example, such an event may take the form of a replacement event (e.g., fluid or component replacement), in which case the predictive model may predict an amount of time before a replacement event needs to occur. In yet other examples, such an event may take the form of a change in asset productivity, in which case the predictive model may predict the productivity of an asset during a particular period of time in the future. In still another example, such an event may take the form of a "leading indicator" event indicating that an asset's behavior that differs from expected asset behaviors, in which case the predictive model may predict the likelihood of one or more leading indicator events occurring in the future. Other examples of predictive models are also possible.

In general, defining the aggregate, predictive model may involve utilizing one or more modeling techniques to generate a model that returns a probability between zero and one, such as a random forest technique, logistic regression technique, or other regression technique, among other modeling techniques. However, other techniques are possible as well.

In one particular example implementation, the predictive model may take the form of one or more predictive models for monitoring the health and outputting a health metric (e.g., "health score") for an asset, which is a single, aggregated metric that indicates whether a failure will occur at a given asset within a given timeframe into the future (e.g., the next two weeks). In particular, a health metric may indicate a likelihood that no failures from a group of failures will occur at an asset within a given timeframe into the future, or a health metric may indicate a likelihood that at least one failure from a group of failures will occur at an asset within a given timeframe into the future.

Depending on the desired granularity of the health metric, the analytics system 108 may be configured to define different predictive models that output different levels of health metrics, each of which may be used as the predictive model in accordance with the present disclosure. For example, the analytics system 108 may define a predictive model that outputs a health metric for the asset as a whole (i.e., an asset-level health metric). As another example, the analytics system 108 may define a respective predictive model that outputs a respective health metric for one or more subsystems of the asset (i.e., subsystem-level health metrics). In some cases, the outputs of each subsystem-level predictive model may be combined to generate an asset-level health metric. Other examples are also possible.

Figure 6:
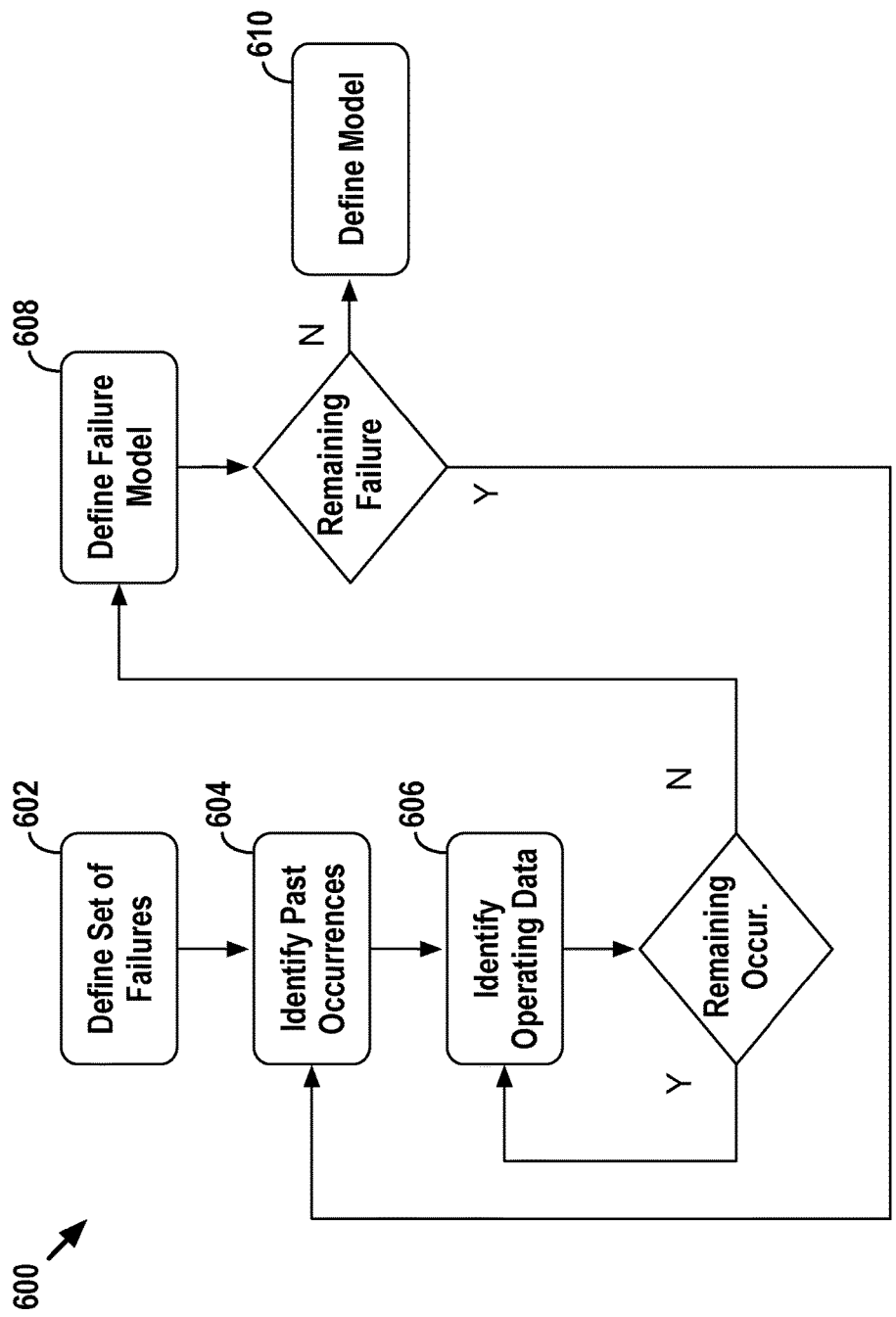
FIG. 6 depicts an example flow diagram of a modeling phase that may be used for defining a predictive model that outputs a health metric.

In general, defining a predictive model that outputs a health metric may be performed in a variety of manners. FIG. 6 is a flow diagram 600 depicting one possible example of a modeling phase that may be used for defining a model that outputs a health metric. For purposes of illustration, the example modeling phase is described as being carried out by the analytics system 108, but this modeling phase may be carried out by other systems as well. One of ordinary skill in the art will appreciate that the flow diagram 600 is provided for sake of clarity and explanation and that numerous other combinations of operations may be utilized to determine a health metric.

As shown in FIG. 6, at block 602, the analytics system 108 may begin by defining a set of the one or more failures that form the basis for the health metric (i.e., the failures of interest). In practice, the one or more failures may be those failures that could render an asset (or a subsystem thereof) inoperable if they were to occur. Based on the defined set of failures, the analytics system 108 may take steps to define a model for predicting a likelihood of any of the failures occurring within a given timeframe in the future (e.g., the next two weeks).

In particular, at block 604, the analytics system 108 may analyze historical operating data for a group of one or more assets to identify past occurrences of a given failure from the set of failures. At block 606, the analytics system 108 may identify a respective set of operating data that is associated with each identified past occurrence of the given failure (e.g., sensor and/or actuator data from a given timeframe prior to the occurrence of the given failure). At block 608, the analytics system 108 may analyze the identified sets of operating data associated with past occurrences of the given failure to define a relationship (e.g., a failure model) between (1) the values for a given set of operating metrics and (2) the likelihood of the given failure occurring within a given timeframe in the future (e.g., the next two weeks). Lastly, at block 610, the defined relationship for each failure in the defined set (e.g., the individual failure models) may then be combined into a model for predicting the overall likelihood of a failure occurring.

As the analytics system 108 continues to receive updated operating data for the group of one or more assets, the analytics system 108 may also continue to refine the predictive model for the defined set of one or more failures by repeating steps 604-610 on the updated operating data.

The functions of the example modeling phase illustrated in FIG. 6 will now be described in further detail. Starting with block 602, as noted above, the analytics system 108 may begin by defining a set of the one or more failures that form the basis for the health metric. The analytics system 108 may perform this function in various manners.

In one example, the set of the one or more failures may be based on one or more user inputs. Specifically, the analytics system 108 may receive from a computing system operated by a user, such as the output system 110, input data indicating a user selection of the one or more failures. As such, the set of one or more failures may be user-defined.

In other examples, the set of the one or more failures may be based on a determination made by the analytics system 108 (e.g., machine-defined). In particular, the analytics system 108 may be configured to define the set of one or more failures, which may occur in a number of manners.

For instance, the analytics system 108 may be configured to define the set of failures based on one or more characteristics of the asset 102. That is, certain failures may correspond to certain characteristics, such as asset type, class, etc., of an asset. For example, each type and/or class of asset may have respective failures of interest.

In another instance, the analytics system 108 may be configured to define the set of failures based on historical data stored in the databases of the analytics system 108 and/or external data provided by the data source 112. For example, the analytics system 108 may utilize such data to determine which failures result in the longest repair-time and/or which failures are historically followed by additional failures, among other examples.

In yet other examples, the set of one or more failures may be defined based on a combination of user inputs and determinations made by the analytics system 108. Other examples are also possible.

At block 604, for each of the failures from the set of failures, the analytics system 108 may analyze historical operating data for a group of one or more assets (e.g., abnormal-behavior data) to identify past occurrences of a given failure. The group of the one or more assets may include a single asset, such as asset 102, or multiple assets of a same or similar type, such as fleet of assets that includes the assets 102 and 104. The analytics system 108 may analyze a particular amount of historical operating data, such as a certain amount of time's worth of data (e.g., a month's worth) or a certain number of data-points (e.g., the most recent thousand data-points), among other examples.

In practice, identifying past occurrences of the given failure may involve the analytics system 108 identifying the type of operating data, such as abnormal-condition data, that indicates the given failure. In general, a given failure may be associated with one or multiple abnormal-condition indicators, such as fault codes. That is, when the given failure occurs, one or multiple abnormal-condition indicators may be triggered. As such, abnormal-condition indicators may be reflective of an underlying symptom of a given failure.

After identifying the type of operating data that indicates the given failure, the analytics system 108 may identify the past occurrences of the given failure in a number of manners. For instance, the analytics system 108 may locate, from historical operating data stored in the databases of the analytics system 108, abnormal-condition data corresponding to the abnormal-condition indicators associated with the given failure. Each located abnormal-condition data would indicate an occurrence of the given failure. Based on this located abnormal-condition data, the analytics system 108 may identify a time at which a past failure occurred.

At block 606, the analytics system 108 may identify a respective set of operating data that is associated with each identified past occurrence of the given failure. In particular, the analytics system 108 may identify a set of sensor and/or actuator data from a certain timeframe around the time of the given occurrence of the given failure. For example, the set of data may be from a particular timeframe (e.g., two weeks) before, after, or around the given occurrence of the failure. In other cases, the set of data may be identified from a certain number of data-points before, after, or around the given occurrence of the failure.

In example implementations, the set of operating data may include sensor and/or actuator data from some or all of the sensors and actuators of the asset 102. For example, the set of operating data may include data from sensors and/or actuators associated with an abnormal-condition indicator corresponding to the given failure.

Figure 7:
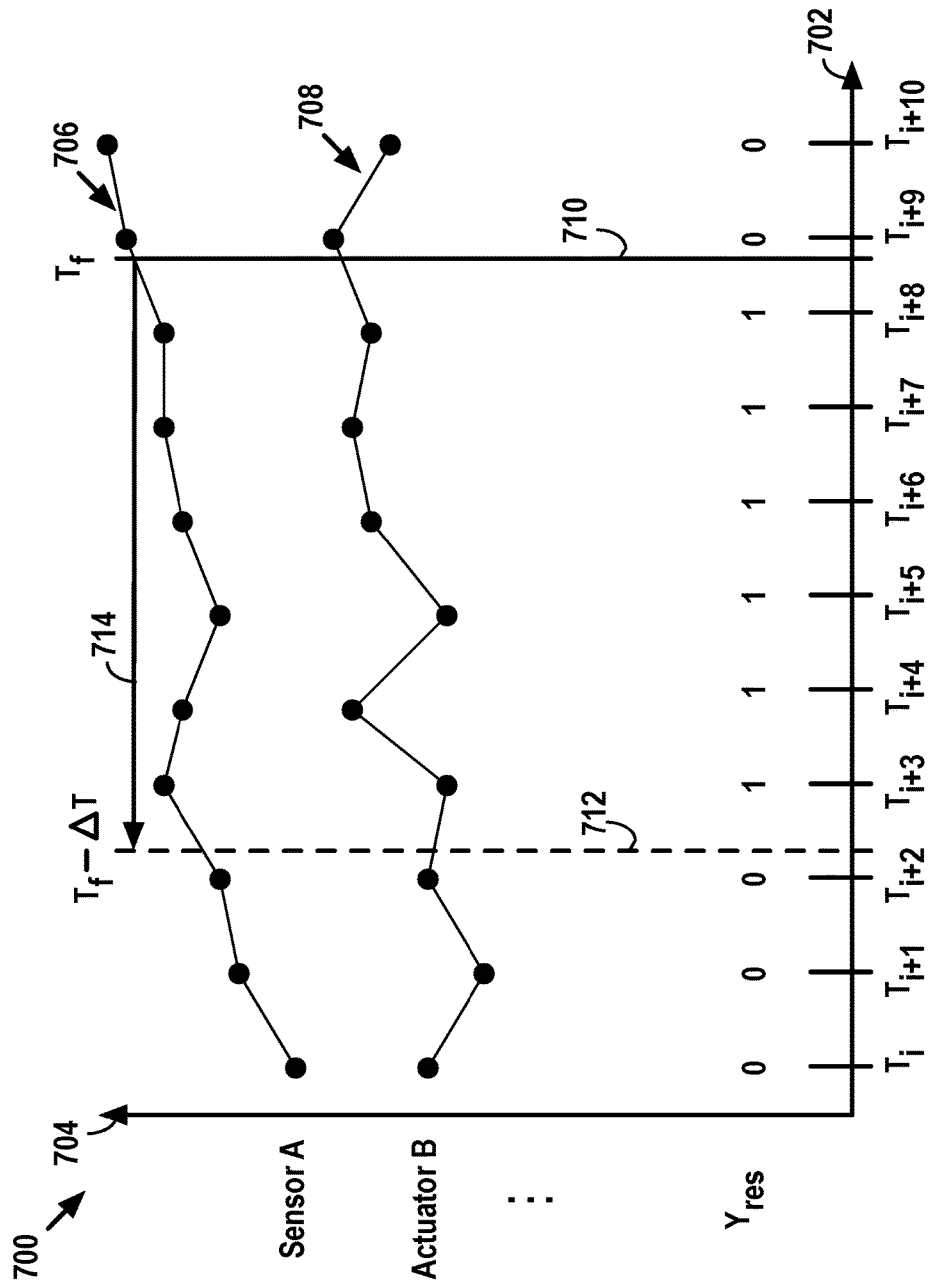
FIG. 7 depicts a conceptual illustration of data utilized to define a model.

To illustrate, FIG. 7 depicts a conceptual illustration of historical operating data that the analytics system 108 may analyze to facilitate defining a model. Plot 700 may correspond to a segment of historical data that originated from some (e.g., Sensor A and Actuator B) or all of the sensors and actuators of the asset 102. As shown, the plot 700 includes time on the x-axis 702, measurement values on the y-axis 704, and sensor data 706 corresponding to Sensor A and actuator data 708 corresponding to Actuator B, each of which includes various data-points representing measurements at particular points in time, $T_i$. Moreover, the plot 700 includes an indication of an occurrence of a failure 710 that occurred at a past time, $T_f$ (e.g., "time of failure"), and an indication of an amount of time 712 before the occurrence of the failure, $\Delta T$, from which sets of operating data are identified. As such, $T_f$–$\Delta T$ defines a timeframe 714 of data-points of interest.

Returning to FIG. 6, after the analytics system 108 identifies the set of operating data for the given occurrence of the given failure (e.g., the occurrence at $T_f$), the analytics system 108 may determine whether there are any remaining occurrences for which a set of operating data should be identified. In the event that there is a remaining occurrence, block 606 would be repeated for each remaining occurrence.

Thereafter, at block 608, the analytics system 108 may analyze the identified sets of operating data associated with the past occurrences of the given failure to define a relationship (e.g., a failure model) between (1) a given set of operating metrics (e.g., a given set of sensor and/or actuator measurements) and (2) the likelihood of the given failure occurring within a given timeframe in the future (e.g., the next two weeks). That is, a given failure model may take as inputs sensor and/or actuator measurements from one or more sensors and/or actuators and output a probability that the given failure will occur within the given timeframe in the future.

In general, a failure model may define a relationship between operating conditions of the asset 102 and the likelihood of a failure occurring. In some implementations, in addition to raw data signals from sensors and/or actuators of the asset 102, a failure model may receive a number of other data inputs, also known as features, which are derived from the sensor and/or actuator signals. Such features may include an average or range of values that were historically measured when a failure occurred, an average or range of value gradients (e.g., a rate of change in measurements) that were historically measured prior to an occurrence of a failure, a duration of time between failures (e.g., an amount of time or number of data-points between a first occurrence of a failure and a second occurrence of a failure), and/or one or more failure patterns indicating sensor and/or actuator measurement trends around the occurrence of a failure. One of ordinary skill in the art will appreciate that these are but a few example features that can be derived from sensor and/or actuator signals and that numerous other features are possible.

In practice, a failure model may be defined in a number of manners. In example implementations, the analytics system 108 may define a failure model by utilizing one or more modeling techniques that return a probability between zero and one, which may take the form of any modeling techniques described above.

In a particular example, defining a failure model may involve the analytics system 108 generating a response variable based on the historical operating data identified at block 606. Specifically, the analytics system 108 may determine an associated response variable for each set of sensor and/or actuator measurements received at a particular point in time. As such, the response variable may take the form of a data set associated with the failure model.

The response variable may indicate whether the given set of measurements is within any of the timeframes determined at block 606. That is, a response variable may reflect whether a given set of data is from a time of interest about the occurrence of a failure. The response variable may be a binary-valued response variable such that, if the given set of measurements is within any of determined timeframes, the associated response variable is assigned a value of one, and otherwise, the associated response variable is assigned a value of zero.

Returning to FIG. 7, a conceptual illustration of a response variable vector, $Y_{res}$, is shown on the plot 700. As shown, response variables associated with sets of measurements that are within the timeframe 714 have a value of one (e.g., $Y_{res}$ at times $T_{i+3}$-$T_{i+8}$), while response variables associated with sets of measurements outside the timeframe 714 have a value of zero (e.g., $Y_{res}$ at times $T_i$-$T_{i+2}$ and $T_{i+9}$-$T_{i+10}$). Other response variables are also possible.

Continuing in the particular example of defining a failure model based on a response variable, the analytics system 108 may train the failure model with the historical operating data identified at block 606 and the generated response variable. Based on this training process, the analytics system 108 may then define the failure model that receives as inputs various sensor and/or actuator data and outputs a probability between zero and one that a failure will occur within a period of time equivalent to the timeframe used to generate the response variable.

In some cases, training with the historical operating data identified at block 606 and the generated response variable may result in variable importance statistics for each sensor and/or actuator. A given variable importance statistic may indicate the sensor's or actuator's relative effect on the probability that a given failure will occur within the period of time into the future.

Additionally or alternatively, the analytics system 108 may be configured to define a failure model based on one or more survival analysis techniques, such as a Cox proportional hazard technique. The analytics system 108 may utilize a survival analysis technique in a manner similar in some respects to the above-discussed modeling technique, but the analytics system 108 may determine a survival time-response variable that indicates an amount of time from the last failure to a next expected event. A next expected event may be either reception of sensor and/or actuator measurements or an occurrence of a failure, whichever occurs first. This response variable may include a pair of values that are associated with each of the particular points in time at which measurements are received. The response variable may then be utilized to determine a probability that a failure will occur within the given timeframe in the future.

In some example implementations, the failure model may be defined based in part on external data, such as weather data, and "hotbox" data, among other data. For instance, based on such data, the failure model may increase or decrease an output failure probability.

In practice, external data may be observed at points in time that do not coincide with times at which asset sensors and/or actuators obtain measurements. For example, the times at which "hotbox" data is collected (e.g., times at which a locomotive passes along a section of railroad track that is outfitted with hot box sensors) may be in disagreement with sensor and/or actuator measurement times. In such cases, the analytics system 108 may be configured to perform one or more operations to determine external data observations that would have been observed at times that correspond to the sensor measurement times.

Specifically, the analytics system 108 may utilize the times of the external data observations and times of the measurements to interpolate the external data observations to produce external data values for times corresponding to the measurement times. Interpolation of the external data may allow external data observations or features derived therefrom to be included as inputs into the failure model. In practice, various techniques may be used to interpolate the external data with the sensor and/or actuator data, such as nearest-neighbor interpolation, linear interpolation, polynomial interpolation, and spline interpolation, among other examples.

Returning to FIG. 6, after the analytics system 108 determines a failure model for a given failure from the set of failures defined at block 602, the analytics system 108 may determine whether there are any remaining failures for which a failure model should be determined. In the event that there remains a failure for which a failure model should be determined, the analytics system 108 may repeat the loop of blocks 604-608. In some implementations, the analytics system 108 may determine a single failure model that encompasses all of the failures defined at block 602. In other implementations, the analytics system 108 may determine a failure model for each subsystem of the asset 102, which may then be utilized to determine an asset-level failure model. Other examples are also possible.

Lastly, at block 610, the defined relationship for each failure in the defined set (e.g., the individual failure models) may then be combined into the model (e.g., the health-metric model) for predicting the overall likelihood of a failure occurring within the given timeframe in the future (e.g., the next two weeks). That is, the model receives as inputs sensor and/or actuator measurements from one or more sensors and/or actuators and outputs a single probability that at least one failure from the set of failures will occur within the given timeframe in the future.

The analytics system 108 may define the health-metric model in a number of manners, which may depend on the desired granularity of the health metric. That is, in instances where there are multiple failure models, the outcomes of the failure models may be utilized in a number of manners to obtain the output of the health-metric model. For example, the analytics system 108 may determine a maximum, median, or average from the multiple failure models and utilize that determined value as the output of the health-metric model.

In other examples, determining the health-metric model may involve the analytics system 108 attributing a weight to individual probabilities output by the individual failure models. For instance, each failure from the set of failures may be considered equally undesirable, and so each probability may likewise be weighted the same in determining the health-metric model. In other instances, some failures may be considered more undesirable than others (e.g., more catastrophic or require longer repair time, etc.), and so those corresponding probabilities may be weighted more than others.

In yet other examples, determining the health-metric model may involve the analytics system 108 utilizing one or more modeling techniques, such as a regression technique. An aggregate response variable may take the form of the logical disjunction (logical OR) of the response variables (e.g., $Y_{res}$ in FIG. 7) from each of the individual failure models. For example, aggregate response variables associated with any set of measurements that occur within any timeframe determined at block 606 (e.g., the timeframe 714 of FIG. 7) may have a value of one, while aggregate response variables associated with sets of measurements that occur outside any of the timeframes may have a value of zero. Other manners of defining the health-metric model are also possible.

In some implementations, block 610 may be unnecessary. For example, as discussed above, the analytics system 108 may determine a single failure model, in which case the health-metric model may be the single failure model.

It should be understood, however, that the health score model disclosed herein is simply one example of a predictive model that may be used to trigger the workflow for adjusting intake operation. Other examples of predictive models may be used as well.

Returning back to FIG. 5, the analytics system 108 may also be configured to define individualized predictive models for assets, which may involve utilizing the aggregate, predictive model as a baseline. The individualization may be based on certain characteristics of assets. In this way, the analytics system 108 may provide a given asset a more accurate and robust predictive model compared to the aggregate predictive model.

In particular, at block 506, the analytics system 108 may be configured to decide whether to individualize the aggregate model defined at block 504 for a given asset, such as the asset 102. The analytics system 108 may carry out this decision in a number of manners.

In some cases, the analytics system 108 may be configured to define individualized predictive models by default. In other cases, the analytics system 108 may be configured to decide whether to define an individualized predictive model based on certain characteristics of the asset 102. For example, in some cases, only assets of certain types or classes, or operated in certain environments, or that have certain health scores may receive an individualized predictive model. In yet other cases, a user may define whether an individualized model is defined for the asset 102. Other examples are also possible.

In any event, if the analytics system 108 decides to define an individualized predictive model for the asset 102, the analytics system 108 may do so at block 508.

At block 508, the analytics system 108 may be configured to define an individualized predictive model in a number of manners. In example implementations, the analytics system 108 may define an individualized predictive model based at least in part on one or more characteristics of the asset 102.

Before defining the individualized predictive model for the asset 102, the analytics system 108 may have determined one or more asset characteristics of interest that form the basis of individualized models. In practice, different predictive models may have different corresponding characteristics of interest.

In general, the characteristics of interest may be characteristics that are related to the aggregate model-workflow pair. For instance, the characteristics of interest may be characteristics that the analytics system 108 has determined influence the accuracy of the aggregate model-workflow pair. Examples of such characteristics may include asset age, asset usage, asset capacity, asset load, asset health (perhaps indicated by an asset health metric, discussed below), asset class (e.g., brand and/or model), and environment in which an asset is operated, among other characteristics.

The analytics system 108 may have determined the characteristics of interest in a number of manners. In one example, the analytics system 108 may have done so by performing one or more modeling simulations that facilitate identifying the characteristics of interest. In another example, the characteristics of interest may have been predefined and stored in the data storage of the analytics system 108. In yet another example, characteristics of interest may have been defined by a user and provided to the analytics system 108 via the output system 110. Other examples are also possible.

In any event, after determining the characteristics of interest, the analytics system 108 may determine characteristics of the asset 102 that correspond to the determined characteristics of interest. That is, the analytics system 108 may determine a type, value, existence or lack thereof, etc. of the asset 102's characteristics that correspond to the characteristics of interest. The analytics system 108 may perform this operation in a number of manners.

For examples, the analytics system 108 may be configured to perform this operation based on data originating from the asset 102 and/or the data source 112. In particular, the analytics system 108 may utilize operating data for the asset 102 and/or external data from the data source 112 to determine one or more characteristics of the asset 102. Other examples are also possible.

Based on the determined one or more characteristics of the asset 102, the analytics system 108 may define an individualized, predictive model by modifying the aggregate model. The aggregate model may be modified in a number of manners. For example, the aggregate model may be modified by changing (e.g., adding, removing, re-ordering, etc.) one or more model inputs, changing one or more sensor and/or actuator measurement ranges that correspond to asset-operating limits (e.g., changing operating limits that correspond to "leading indicator" events), changing one or more model calculations, weighting (or changing a weight of) a variable or output of a calculation, utilizing a modeling technique that differs from that which was utilized to define the aggregate model, and/or utilizing a response variable that differs from that which was utilized to define the aggregate model, among other examples.

In practice, individualizing the aggregate model may depend on the one or more characteristics of the given asset. In particular, certain characteristics may affect the modification of the aggregate model differently than other characteristics. Further, the type, value, existence, or the like of a characteristic may affect the modification as well. For example, the asset age may affect a first part of the aggregate model, while an asset class may affect a second, different part of the aggregate model. And an asset age within a first range of ages may affect the first part of the aggregate model in a first manner, while an asset age within a second range of ages, different from the first range, may affect the first part of the aggregate model in a second, different manner. Other examples are also possible.

In some implementations, individualizing the aggregate model may depend on considerations in addition to or alternatively to asset characteristics. For instance, the aggregate model may be individualized based on sensor and/or actuator readings of an asset when the asset is known to be in a relatively good operating state (e.g., as defined by a mechanic or the like). More particularly, in an example of a leading-indicator predictive model, the analytics system 108 may be configured to receive an indication that the asset is in a good operating state (e.g., from a computing device operated by a mechanic) along with operating data from the asset. Based at least on the operating data, the analytics system 108 may then individualize the leading-indicator predictive model for the asset by modifying respective operating limits corresponding to "leading indicator" events. Other examples are also possible.

It should also be understood that, in some example implementations, the analytics system 108 may be configured to define an individualized predictive model for a given asset without first defining an aggregate predictive model. Other examples are also possible.

Once a predictive model is defined, the analytics system 108 may also be configured to update that model based on new asset data. For instance, based on new historical data received from assets or other data sources, the analytics system 108 may modify an aggregate and/or individualized model for an asset. The analytics system 108 could perform this updating function periodically (e.g., daily, weekly, monthly, etc.) and/or in response to some triggering event (e.g., the receipt of new historical data or the occurrence of an event). The analytics system 108 may update the predictive model in other manners as well.

It should also be understood that devices and/or systems other than analytics system 108 may be configured to individualize and modify the predictive models. For example, if an asset includes a local analytics device that is configured to receive and execute a predictive model, then this local analytics device could also be configured to individualize and/or modify a predictive model either alone or in combination with the analytics system 108. The operation of a representative local analytics device is disclosed in further detail in U.S. application Ser. No. 14/963,207, which is incorporated by reference herein in its entirety.

2. Workflow for Adjusting Intake Operation

As noted above, the predictive model disclosed above may correspond to a workflow for adjusting intake operation based on the predictive model's output. This intake workflow may take various forms.

According to one embodiment, an intake workflow may involve modifying the storage location of data ingested from a given asset based on the predictive model. For example, when a predictive model indicates that at least one event from a given group of events is threshold likely to occur at the given asset within a particular period of time in the future, the workflow may be configured to route data ingested from a given asset to a more durable, reliable, and/or robust storage location. Other examples are possible as well.

According to another embodiment, an intake workflow may involve modifying the set of data variables ingested from a given asset based on a predictive model. For instance, when a predictive model indicates that at least one event from a given group of events is threshold likely to occur at the given asset within a particular period of time in the future, the workflow may be configured to expand the set of data ingested from a given asset to include additional data variables (e.g., data streams from additional sensors/actuators at the asset). These additional data variables to be ingested could be predefined, and/or could be defined based on the type and/or output of the predictive model that triggers the intake workflow. For instance, the data intake system may initially be configured to intake a core set of data variables (e.g., temperature, speed, location, etc.), and the intake workflow may then be configured to cause the data intake system to intake additional data variables that relate to a particular type of event that is predicted to occur in the future. As one representative example, if an event associated with an asset's engine is predicted to occur in the future, the intake workflow may cause the data intake system to intake additional data variables that relate to the asset's engine (e.g., voltage, oil pressure, torque, etc.). Many other examples are possible as well.

According to yet another embodiment, an intake workflow may involve modifying the data ingestion rate for a given asset based on a predictive model. For instance, when a predictive model indicates that at least one event from a given group of events is threshold likely to occur at the given asset within a particular period of time in the future, the workflow may be configured to increase the rate at which data is ingested from a given asset. As one representative example, the intake workflow may be configured to increase the data rate by causing the data intake system to switch from a first sampling frequency (e.g., 10 MHz) to a second sampling frequency (e.g., 1 MHz). As another representative example, the intake workflow may be configured to increase the data rate by causing the data intake system to change the amount of received asset data that is stored from a first amount (e.g., every $10^{th}$ data point) to a second amount (e.g., every $2^{nd}$ data point). As yet another representative example, the intake workflow may be configured to increase the data rate by causing the data intake system to switch from a first sampling scheme (e.g., periodic sampling every 15 minutes) to a second sampling scheme (e.g., sampling in response to triggering events such as detecting that the output of the corresponding predictive model exceeds a threshold value). Other examples are possible as well.

It should be understood that two or more of these modification may also be combined into a single intake workflow. Further, it should be understood that an intake workflow may involve other actions for adjusting the analytics system's intake process as well.

An intake workflow such as those described above may also be defined in a variety of manners. In one example, the aggregate workflow may be user defined. Specifically, a user may operate a computing device that receives user inputs indicating selection of certain workflow actions, and the computing device may provide to the analytics system 108 data indicating such selections. Based on this data, the analytics system 108 may then define the workflow.

In another example, the workflow may be machine-defined. In particular, the analytics system 108 may perform various functions, such as simulations, to determine a workflow that may facilitate determining a cause of the probability output by the predictive model and/or preventing an occurrence of an event predicted by the model. Other examples of defining the workflow are also possible.

In defining the workflow corresponding to the predictive model, the analytics system 108 may also define triggers for the workflow. As an example, a workflow trigger may take the form of a threshold value (or range of values) for the predictive model's output (e.g., a health metric below 10%). As another example, a workflow trigger may take the form of a threshold rate of change for the predictive model's output. As another example, a workflow trigger may take the form of a threshold amount of time that a predictive model's output has met a threshold value. Other examples are possible as well. Further, in some cases, a workflow may also have multiple triggers (e.g., multiple threshold values), each of which may cause a different action or actions to occur. It should also be understood that the one or more thresholds may be configurable.

As with the predictive model described above, the workflow for adjusting the intake operation for a given asset may either take the form of an aggregate workflow or an individualized workflow. In this respect, the analytics system 108 (and/or an asset's local analytics device) could define an individualized workflow for the given asset using techniques similar to those described above for defining an individualized predictive model (e.g., by modifying an aggregate workflow based on one or more characteristics of the given asset).

Further, as with the predictive model, the intake workflow may be updated based on new asset data. For instance, based on new data received from assets or other data sources, the analytics system 108 (and/or an asset's local analytics device) may modify an aggregate and/or individualized intake workflow (e.g., by adjusting the storage location for ingested data, the set of data variables to be ingested, and/or the ingestion rate associated with the workflow). This updating function could be performed periodically (e.g., daily, weekly, monthly, etc.) and/or in response to some triggering event (e.g., the receipt of new historical data or the occurrence of an event). The workflow could be updated in other manners as well.

It should also be understood that the intake workflows described above could be paired with and triggered based on certain operating data received from an asset, rather than the output of a predictive model. In one implementation, for instance, an intake workflow may be triggered based on sensor data received from the asset. As one such example, an intake workflow may be configured such that, if the analytics system 108 determines that a given sensor's output satisfies a threshold condition (e.g., a threshold that represents an anomalous value), the intake workflow may then cause the data intake system to adjust its intake operation for the asset (e.g., by changing intake storage locations, expanding the set of intake data variables, and/or increasing the intake data rate). In another implementation, an intake workflow may be triggered based on abnormal-condition indicators received from the asset. As one such example, an intake workflow may be configured such that, if the analytics system 108 receives certain abnormal-condition indicators (or certain combinations of abnormal-condition indicators) from an asset, the intake workflow may then cause the data intake system to adjust its intake operation for that asset. The intake workflows could be triggered based on other factors as well.

C. Execution of the Model-Workflow Pair

Once the model-workflow pair disclosed above is defined by the analytics system 108, that model-workflow pair may then be deployed for runtime execution. For instance, in a preferred implementation, the analytics system 108 may be configured to operate in accordance with the model-workflow pair.

According to this implementation, the analytics system 108 may begin by operating in a first mode in which the analytics system's data intake system 402 ingests received data (e.g., sensor and/or actuator signals) for various assets, such as the asset 102, according to a default set of intake parameters.

While the data intake system 402 operates in the first mode, the analytics system's data science system 404 may then input at least a portion of the ingested data into the predictive model for determining the likelihood that at least one event of a given group of events (e.g., failure events) may occur at the asset within a given period of time in the future. The data science system 404 may then eventually determine, based on this predictive model, that the likelihood of at least one such event occurring at the asset within the given period of time in the future satisfies a first threshold condition. For example, the data science system 404 may determine that a health score for the asset 102 is at or below 10%.

This determination may then trigger an intake workflow, which may cause the analytics system 108 to transition from operating in the first mode to operating in a second mode in which the analytics system's data intake system 402 ingests data for asset 102 (and perhaps other associated assets) according to a set of intake parameters that includes at least one modified intake parameter. For instance, in practice, this intake workflow may cause the data science system 404 to signal to the data intake system 402 to transition to a different operating mode and/or modify an intake parameter. However, other implementations are possible as well. After the intake workflow is triggered, the analytics system 108 may then begin ingesting data in accordance with the modified intake parameter(s).

The analytics system's data science system 404 may thereafter continue to input at least a portion of the ingested data into the predictive model, and at some point, may determine that the likelihood of at least one such event occurring at the asset within the given period of time in the future satisfies a second threshold condition. In response, the analytics system 108 may then transition into another mode and/or further modify the set of intake parameters.

At some later time, the data science system 404 may also determine, based on the predictive model, that the likelihood of at least one event of the give group of events occurring at the asset within the given period of time in the future no longer satisfies the first threshold condition. In response, the analytics system 108 may transition from operating in the second mode back to operating in the first mode.

As noted above, when transitioning between operating modes, the data intake system 402 may modify various different intake parameters. According to one implementation, the data intake system 402 may modify the storage location of ingested data from a default storage location to a modified storage location. For instance, in a first mode, the data intake system 402 may operate to store intake data in a first storage location (e.g., a first one of databases 406), while in a second operating mode, the data intake system 402 may operate to store data in a second storage location (e.g., a second one of databases 406). In practice, these two storage locations will preferably have different storage characteristics. For example, the second storage location may include a data storage that is more durable, reliable, and/or robust than the first data storage location. As another example, the second storage location may include a higher data storage rate than the first storage location, which may better accommodate a higher data intake rate or an expanded set of data variables being ingested. Also, in some embodiments, one of the first and second storage locations may be disposed external to the analytics system 108 at the same or a different geographic location from the analytics system 108 (e.g., at a remote data server). It should also be understood that, in some operating modes, the data intake system 402 may be configured to store intake data at multiple different storage locations (e.g., a first location and a second location).

The modified storage location may be selected in various manners. In one example, the modified storage location may be a single, fixed storage location that is selected as part of the workflow definition. In another example, the modified storage location could vary depending on factors such as the type of predictive model, the predictive model's output value, the workflow's threshold value, and/or the asset's characteristics, among other factors. The modified storage location may be selected in other manners as well.

According to another implementation, the data intake system 402 may modify the set of data variables that are ingested, from a default data set to a modified data set. For example, an intake workflow may cause the data intake system 402 to expand the set of data variables that are ingested for an asset from a first set of data variables (e.g., data variables corresponding to sensors A, B and C of the asset) to a larger, second set of data variables (e.g., data variables corresponding to sensors A, B, and C as well as sensor D of the asset). In another example, an intake workflow could cause the data intake system 402 to change the set of data variables that are ingested for an asset from a first set of data variables (e.g., data variables corresponding to sensors A, B and C of the asset) to a different, second set of data variables (e.g., data variables corresponding to sensors D, E and F of the asset). Other examples are possible as well.

The modified data set may be selected in various manners. In one example, the modified data set may be a fixed set of data variables that is selected as part of the workflow definition. In another example, the modified data set may vary depending on factors such as the type of predictive model, the predictive model's output value, the workflow's threshold value, and/or the asset's characteristics, among other factors. The modified data set may be selected in other manners as well.

According to yet another implementation, the data intake system 402 may modify the intake rate, from a default rate to a modified rate. For example, the data intake system 402 may modify the intake rate by increasing or decreasing a sample rate of the data received from an asset. As another example, the data intake system 402 may modify the intake rate by changing the amount of received asset data that is stored (e.g., if a given data variable is received at a rate of 100 data points/second, the system could store every $10^{th}$ value in a first mode and store every $2^{nd}$ value in a second mode). Other examples are possible as well.

The modified rate may be selected in various manners. In one example, the modified rate may be a fixed rate that is selected as part of the workflow definition. In another example, the modified rate may be a variable rate that may be dependent on factors such as the predictive model's output value, the workflow's threshold value, and/or the asset's characteristics, among other factors. The modified rate may be selected in other manners as well.

It should also be understood that devices and/or systems other than analytics system 108 may be configured to execute (or assist with the execution of) the predictive model and/or the corresponding workflow for modifying intake operation. For example, in line with the discussion above, an asset could include a local analytics device 220 (or the like) that may be configured to execute the predictive model for modifying intake operation, the workflow for modifying intake operation, or both.

In one implementation, for instance, the analytics system 108 may be configured to execute the predictive model and then signal to an asset, which may in turn be configured to execute the corresponding workflow for modifying intake operation based on the signal from the analytics system 108. According to this implementation, the asset may carry out functions before transmitting the operating data that may result in a modification of the analytics system's intake of that data (e.g., by adjusting the transmission data set, the transmission data rate, the transmission channel, or the like).

In another implementation, the asset may be configured to execute the predictive model and then signal to the analytics system 108, which may in turn be configured to execute the corresponding workflow for modifying intake operation based on the signal from the asset.

In yet another implementation, the asset may be configured to execute both the predictive model and the corresponding workflow for modifying intake operation. According to this implementation, as above, the asset may carry out functions before transmitting the operating data that may result in a modification of in the analytics system's intake of that data.

As noted above, the operation of a representative local analytics device is disclosed in further detail in U.S. application Ser. No. 14/963,207, which is incorporated by reference herein in its entirety.

V. EXAMPLE METHOD

Figure 8:
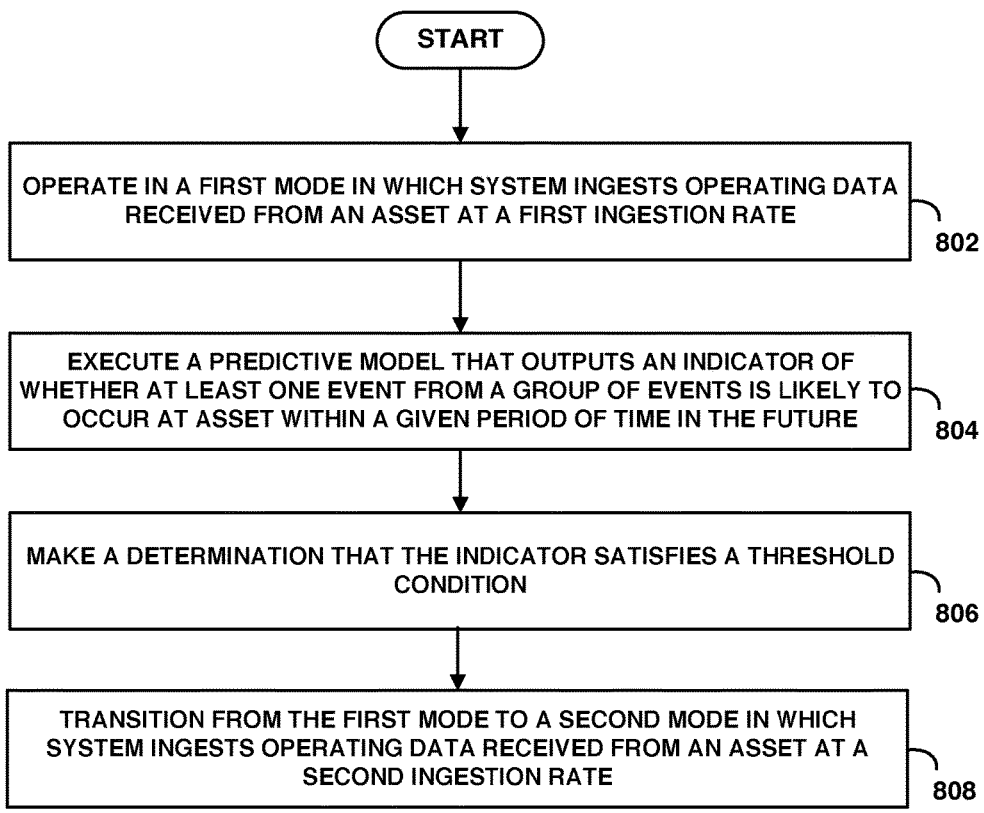
FIG. 8 depicts a flow diagram of an example method for modifying data ingestion rate based on a predictive model.

Turning now to FIG. 8, a flow diagram is depicted illustrating functions that can be carried out in accordance with an example method 800 for modifying the data ingestion rate for an asset based on a predictive model. For purposes of illustration only, these functions are described as being carried out by the analytics system 108, but it should be understood that one or more of these functions may be carried out by other devices or systems (e.g., a local analytics device 220 of an asset). It should also be understood that certain functions could be added to this example method 800 and/or that certain functions described below could be modified or removed from the example method 800.

At block 802, the example method 800 may involve the analytics system 108 operating in a first mode in which the analytics system 108 is configured to ingest operating data received from a given asset at a first ingestion rate. While operating in this first mode, the analytics system 108 may receive operating data for the given asset (e.g., sensor data, actuator data, abnormal-condition data, etc.) and then ingest at least a portion of the received operating data via the data intake system 402 at the first ingestion rate.

At block 804, the method 800 may involve the analytics system 108 executing a predictive model that outputs an indicator of whether at least one event from a group of events is likely to occur at the given asset within a given period of time in the future (e.g. a health metric indicating whether at least one failure from the group of failures is likely to occur at the given asset within the given period of time in the future).

At block 806, the method 800 may involve the analytics system 108 making a determination that the indicator satisfies a threshold condition. For instance, if the predictive model outputs a probability that no event from the group of events is likely to occur at the given asset within the given period of time in the future, the analytics system 108 may determine that the probability is at or below a threshold value. On the other hand, if the predictive model outputs a probability of at least one event from the group of events occurring at the given asset within the given period of time in the future, the analytics system 108 may determine that the probability is at or above a threshold value. Other implementations are possible as well.

At block 808, the method 800 may involve the analytics system 108 transitioning from the first mode of block 802 to a second mode in which the analytics system 108 is configured to ingest operating data from the given asset at a second ingestion rate that differs from the first ingestion rate (e.g., a higher ingestion rate). After transitioning to operating in the second mode, the analytics system 108 may receive operating data for the given asset and then ingest at least a portion of the received operating data via the data intake system 402 at the second ingestion rate.

VI. CONCLUSION

Example embodiments of the disclosed innovations have been described above. Those skilled in the art will understand, however, that changes and modifications may be made to the embodiments described without departing from the true scope and sprit of the present invention, which will be defined by the claims.

Further, to the extent that examples described herein involve operations performed or initiated by actors, such as "humans", "operators", "users" or other entities, this is for purposes of example and explanation only. The claims should not be construed as requiring action by such actors unless explicitly recited in the claim language.

The invention claimed is:

1. A computing system comprising:
a network interface configured to receive data from a plurality of assets;
a data intake system configured to ingest data received from the plurality of assets;
at least one processor;
a non-transitory computer-readable medium; and
program instructions stored on the non-transitory computer-readable medium that are executable by the at least one processor to cause the computing system to:
based on historical operating data for a plurality of assets, define a predictive model that is configured to (a) receive sensor data for an asset as input, (b) for each of at least two failure types from a group of failure types related to mechanical operation, make a respective prediction of whether the failure type is likely to occur at the asset in the future, and (c) based on the respective predictions, determine and output a health metric indicating whether at least one failure type from the group of failure types related to mechanical operation is predicted to occur at the asset in the future, wherein the historical operating data comprises (i) historical abnormal-condition data for the plurality of assets that indicates past occurrences of abnormal conditions that are associated with the group of failure types and (ii) historical sensor data for the plurality of assets that indicates sensor measurements associated with the past occurrences of abnormal conditions;
operate in a first mode in which the data intake system ingests operating data received from a given asset of the plurality of assets at a first ingestion rate, wherein the operating data comprises data related to the mechanical operation of the given asset that includes abnormal-condition data and sensor data;
while operating in the first mode, (a) receive operating data from the given asset; and (b) ingest at least a portion of the received operating data at the first ingestion rate, wherein the ingested portion of the received operating data includes ingested sensor data for the given asset;
apply the predictive model to the ingested sensor data and thereby determine a health metric for the given asset that indicates whether at least one failure type from the group of failure types related to mechanical operation is predicted to occur at the given asset in the future;
compare the health metric for the given asset to a threshold condition that defines whether an asset is considered to be in a state of impending failure and thereby make a determination that the health metric satisfies the threshold condition such that the given asset is considered to be in a state of impending failure;
in response to the determination, transition from operating in the first mode to operating in a second mode in which the data intake system ingests operating data from the given asset at a second ingestion rate that is higher than the first ingestion rate; and
while operating in the second mode, (a) receive operating data from the given asset and (b) ingest at least a portion of the received operating data at the second ingestion rate, wherein the ingested operating data comprises data related to the mechanical operation of the given asset that includes abnormal-condition data and sensor data.

2. The computing system of claim 1, wherein the health metric indicating whether at least one failure type from the group of failure types related to mechanical operation is predicted to occur at the given asset in the future comprises a probability that no failure type from the group of failure types related to mechanical operation is predicted to occur at the given asset in the future, and wherein the determination that the indicator satisfies the threshold condition comprises a determination that the probability is at or below a threshold value.

3. The computing system of claim 1, wherein the health metric indicating whether at least one failure type from the group of failure types related to mechanical operation of the given asset is predicted to occur at the given asset in the future comprises a probability that at least one f failure type from the group of failure types related to mechanical operation of an asset is predicted to occur at the given asset in the future, and wherein the determination that the indicator satisfies the threshold condition comprises a determination that the probability is at or above a threshold value.

4. The computing system of claim 1, wherein the second ingestion rate comprises a variable rate that is determined based on the health score.

5. The computing system of claim 1, wherein the given asset comprises a transportation machine, an industrial machine, or a utility machine.

6. The computing system of claim 1, wherein the second ingestion rate comprises a variable rate that is determined based on the comparison of the health metric to the threshold condition.

7. The computing system of claim 1, wherein the second ingestion rate comprises a variable rate that is determined based on one or more characteristics of the given asset.

8. A non-transitory computer-readable medium having instructions stored thereon that are executable to cause a computing system to:
based on historical operating data for a plurality of assets, define a predictive model that is configured to (a) receive sensor data for an asset as input, (b) for each of at least two failure types from a group of failure types related to mechanical operation, make a respective prediction of whether the failure type is likely to occur at the asset in the future, and (c) based on the respective predictions, determine and output a health metric indicating whether at least one failure type from the group of failure types related to mechanical operation is predicted to occur at the asset in the future, wherein the historical operating data comprises (i) historical abnormal-condition data for the plurality of assets that indicates past occurrences of abnormal conditions that are associated with the group of failure types and (ii) historical sensor data for the plurality of assets that indicates sensor measurements associated with the past occurrences of abnormal conditions;
operate in a first mode in which the computing system ingests operating data received from a given asset of the plurality of assets at a first ingestion rate, wherein the operating data comprises data related to the mechanical operation of the given asset that includes abnormal-condition data and sensor data;
while operating in the first mode, (a) receive operating data from the given asset, and (b) ingest at least a portion of the received operating data at the first ingestion rate, wherein the ingested portion of the received operating data includes ingested sensor data for the given asset;

apply the predictive model to the ingested sensor data and thereby determine a health metric for the given asset that indicates whether at least one failure type from the group of failure types related to mechanical operation is predicted to occur at the given asset in the future;

compare the health metric for the given asset to a threshold condition that defines whether an asset is considered to be in a state of impending failure and thereby make a determination that the health metric satisfies the threshold condition such that the given asset is considered to be in a state of impending failure;

in response to the determination, transition from operating in the first mode to operating in a second mode in which the computing system ingests operating data from the given asset at a second ingestion rate that is higher than the first ingestion rate; and while operating in the second mode, (a) receive operating data from the given asset and (b) ingest at least a portion of the received operating data at the second ingestion rate, wherein the ingested operating data comprises data related to the mechanical operation of the given asset that includes abnormal-condition data and sensor data.

9. The non-transitory computer-readable medium of claim 8, wherein the health metric indicating whether at least one failure type from the group of failure types related to mechanical operation is predicted to occur at the given asset in the future comprises a probability that no failure type from the group of failure types related to mechanical operation is predicted to occur at the given asset in the future, and wherein the determination that the indicator satisfies the threshold condition comprises a determination that the probability is at or below a threshold value.

10. The non-transitory computer-readable medium of claim 8, wherein the health metric indicating whether at least one failure type from the group of failure types related to mechanical operation of the given asset is predicted to occur at the given asset in the future comprises a probability that at least one f failure type from the group of failure types related to mechanical operation of an asset is predicted to occur at the given asset in the future, and wherein the determination that the indicator satisfies the threshold condition comprises a determination that the probability is at or above a threshold value.

11. The non-transitory computer-readable medium of claim 8, wherein the given asset comprises a transportation machine, an industrial machine, or a utility machine.

12. The non-transitory computer-readable medium of claim 8, wherein the second ingestion rate comprises a variable rate that is determined based on the health score.

13. The non-transitory computer-readable medium of claim 8, wherein the second ingestion rate comprises a variable rate that is determined based on the comparison of the health metric to the threshold condition.

14. A computer-implemented method comprising:

based on historical operating data for a plurality of assets, defining a predictive model that is configured to (a) receive sensor data for an asset as input, (b) for each of at least two failure types from a group of failure types related to mechanical operation, make a respective prediction of whether the failure type is likely to occur at the asset in the future, and (c) based on the respective predictions, determine and output a health metric indicating whether at least one failure type from the group of failure types related to mechanical operation is predicted to occur at the asset in the future, wherein the historical operating data comprises (i) historical abnormal-condition data for the plurality of assets that indicates past occurrences of abnormal conditions that are associated with the group of failure types and (ii) historical sensor data for the plurality of assets that indicates sensor measurements associated with the past occurrences of abnormal conditions;

operating a computing system in a first mode in which the computing system ingests operating data received from a given asset of the plurality of assets at a first ingestion rate, wherein the operating data comprises data related to the mechanical operation of the given asset that includes abnormal-condition data and sensor data;

while operating the computing system in the first mode, (a) receiving operating data from the given asset, and (b) ingesting at least a portion of the received operating data at the first ingestion rate, wherein the ingested portion of the received operating data includes ingested sensor data for the given asset;

applying the predictive model to the ingested sensor data and thereby determining a health metric for the given asset that indicates whether at least one failure type from the group of failure types related to mechanical operation is predicted to occur at the given asset in the future;

comparing the health metric for the given asset to a threshold condition that defines whether an asset is considered to be in a state of impending failure and thereby making a determination that the indicator satisfies the threshold condition such that the given asset is considered to be in a state of impending failure;

in response to the determination, transitioning the computing system from operating in the first mode to operating in a second mode in which the computing system ingests operating data from the given asset at a second ingestion rate that is higher than the first ingestion rate; and while operating the computing system in the second mode, (a) receiving operating data from the given asset and (b) ingesting at least a portion of the received operating data at the second ingestion rate, wherein the ingested operating data comprises data related to the mechanical operation of the given asset that includes abnormal-condition data and sensor data.

15. The computer-implemented method of claim 14, wherein the health metric indicating whether at least one failure type from the group of failure types related to mechanical operation is predicted to occur at the given asset in the future comprises a probability that no failure type from the group of failure types related to mechanical operation is predicted to occur at the given asset in the future, and wherein the determination that the indicator satisfies the threshold condition comprises a determination that the probability is at or below a threshold value.

16. The computer-implemented method of claim 14, wherein the health metric indicating whether at least one failure type from the group of failure types related to mechanical operation of the given asset is predicted to occur at the given asset in the future comprises a probability that at least one f failure type from the group of failure types related to mechanical operation of an asset is predicted to occur at the given asset in the future, and wherein the determination that the indicator satisfies the threshold condition comprises a determination that the probability is at or above a threshold value.

17. The computer-implemented method of claim 14, wherein the given asset comprises a transportation machine, an industrial machine, or a utility machine.

18. The computer-implemented method of claim 14, wherein the second ingestion rate comprises a variable rate that is determined based on the health score.

19. The computer-implemented method of claim 14, wherein the second ingestion rate comprises a variable rate that is determined based on the comparison of the health metric to the threshold condition.

20. The computer-implemented method of claim 14, wherein the second ingestion rate comprises a variable rate that is determined based on one or more characteristics of the given asset.

* * * * *